United States Patent
Han et al.

(10) Patent No.: US 10,014,089 B2
(45) Date of Patent: Jul. 3, 2018

(54) LIQUID PRECURSOR COMPOSITIONS, PREPARATION METHODS THEREOF, AND METHODS FOR FORMING LAYER USING THE COMPOSITION

(71) Applicant: UP CHEMICAL CO., LTD., Pyeongtaek-si (KR)

(72) Inventors: Won Seok Han, Anseong-si (KR); Wonyong Koh, Daejeon (KR)

(73) Assignee: UP CHEMICAL CO., LTD., Pyeongtaek-si (KR)

(*) Notice: Subject to any disclaimer, the term of this patent is extended or adjusted under 35 U.S.C. 154(b) by 44 days.

(21) Appl. No.: 15/199,705

(22) Filed: Jun. 30, 2016

(65) Prior Publication Data
US 2016/0314980 A1    Oct. 27, 2016

Related U.S. Application Data

(63) Continuation of application No. PCT/KR2015/005945, filed on Jun. 12, 2015.

(30) Foreign Application Priority Data

Jun. 13, 2014  (KR) .................. 10-2014-0072274

(51) Int. Cl.
*H01B 1/02* (2006.01)
*C07F 15/06* (2006.01)
(Continued)

(52) U.S. Cl.
CPC .............. *H01B 1/02* (2013.01); *C07F 15/065* (2013.01); *C09D 11/52* (2013.01); *C23C 16/18* (2013.01);
(Continued)

(58) Field of Classification Search
CPC ... H01B 1/02; H01B 1/08; H01B 1/20; H01B 1/22; C09D 5/24; C09D 11/52;
(Continued)

(56) References Cited

U.S. PATENT DOCUMENTS 9,353,437 B2 * 5/2016 Han ................. C23C 16/18
2007/0160761 A1  7/2007 Han
(Continued)

FOREIGN PATENT DOCUMENTS

KR   10-2012-0053479      5/2012
KR   10-2014-0067147      6/2014
(Continued)

OTHER PUBLICATIONS

Kaltsoyannis "Covalency in metal complexes of 1,4=diazabutadiene (dab). A density functional investigation of the electronic structures of [M(dab),] (M=Li, Ga or Co) and [Th(NH3)(NH2),(dab)]", J. Chem. Soc., Dalton Trans., pp. 1583-1589 (1996).*
(Continued)

*Primary Examiner* — Harold Pyon
*Assistant Examiner* — Matthew R Diaz
(74) *Attorney, Agent, or Firm* — Knobbe, Martens, Olson & Bear LLP

(57) ABSTRACT

Liquid precursor compositions are provided, along with methods of preparing the liquid precursor compositions, and methods for forming layers using the liquid precursor composition, for example in vapor deposition processes such as CVD and ALD. In some embodiments, the liquid precursor compositions comprise a metal compound of the formula $M(DAD)_2$, where M is Co or Ni and DAD is a diazadiene ligand.

13 Claims, 36 Drawing Sheets

(51) Int. Cl.
*C23C 16/18* (2006.01)
*H01B 1/08* (2006.01)
*C09D 11/52* (2014.01)
*C23C 16/06* (2006.01)
*C23C 16/455* (2006.01)
*H01L 21/285* (2006.01)

(52) U.S. Cl.
CPC .............. *H01B 1/08* (2013.01); *C23C 16/06* (2013.01); *C23C 16/45553* (2013.01); *H01L 21/28556* (2013.01)

(58) Field of Classification Search
CPC ........ C07F 15/00; C07F 15/04; C07F 15/045; C07F 15/06; C07F 15/065; C07F 13/00; C07F 13/005
USPC ....... 252/500, 518.1, 519.2, 521.2; 556/138; 427/252
See application file for complete search history.

(56) References Cited

U.S. PATENT DOCUMENTS

| | | | |
|---|---|---|---|
| 2009/0321733 A1* | 12/2009 | Gatineau | C01G 23/00 257/43 |
| 2013/0164456 A1* | 6/2013 | Winter | C23C 16/34 427/535 |
| 2013/0251903 A1 | 9/2013 | Reuter et al. | |
| 2015/0105573 A1* | 4/2015 | Romero | C07F 15/045 556/32 |
| 2015/0170961 A1* | 6/2015 | Romero | H01L 21/76838 438/641 |
| 2016/0122867 A1 | 5/2016 | Han et al. | |
| 2016/0152650 A1* | 6/2016 | Winter | C07F 15/045 427/255.28 |

FOREIGN PATENT DOCUMENTS

| | | | |
|---|---|---|---|
| WO | WO 2012027357 A2 * | 3/2012 | ............ C23C 16/34 |
| WO | WO 2012067439 A2 * | 5/2012 | ............ C23C 16/18 |
| WO | WO 2013/046155 | 4/2013 | |
| WO | WO 2013/046157 | 4/2013 | |

OTHER PUBLICATIONS

Khusniyarov et al., "Molecular and Electronic Structures of Homoleptic Nickel and Cobalt Complexes with Non-Innocent Bulky Diimine Ligands Derived from Fluorinated 1,4-Diaza-1,3-butadiene (DAD) and Bis(arylimino)acenaphthene (BIAN)", Eur. J. Inorg. Chem., pp. 2985-2996 (2006).*
Muresan et al., "Neutral bis(1,4-diaza-1,3-butadiene)nickel complexes and their corresponding monocations: molecular and electronic structures. A combined experimental and density functional theoretical study", Dalton Trans., pp. 4390-4398 (2007).*
English Translation of IDS Reference Svoboda et al., "Bis(diazadien)metall(O)-Komplexe, III. Nickel(O)-bis(chelate) mit aliphatischen N-Substituenten/Bis(diazadien)metal(O) Complexes, III. Nickel(O)-bis(chelates) with Aliphatic N-Substituents", Zeitschrift fur Naturforchung B., 36b, 814-822 (1981).*
Analytical grade. Segen's Medical Dictionary. (2011, retrieved Jan. 31, 2017 from http://medical-dictionary.thefreedictionary.com/analytical+grade).*
International Search Report of PCT/KR2015/005945 dated Sep. 18, 2015.
Kirchmann et al., "Octahedral Coordination Compounds of the Ni, Pd, Pt Triad", Angew. Chem. Int. Ed., Dec. 20, 2007, vol. 47, No. 5, pp. 963-966.
Svoboda et al., "Bis(diazadien)metall(O)-Komplexe, III. Nickel(O)-bis(chelate) mit aliphatischen N-Substituenten/ Bis(diazadien)metal(O) Complexes, III. Nickel(O)-bis(chelates) with Aliphatic N-Substituents", Zeitschrift für Naturforschung B., Jun. 2014, vol. 36, Issue 7, pp. 814-822.
Tate et al., "A Novel Acetylenic Complex of Tungsten(0) Carbonyl", J. Am. Chem. Soc., 1963, 85 (14), pp. 2174-2175.

* cited by examiner

FIG. 1

Reacting a mixture containing a halogenated metal compound represented by $MX_2$ or halogenated metal complex compound represented by $ZMX_2$, a diazadiene ligand compound (DAD compound), and an alkali metal in a solvent,
wherein, in forming the mixture, the DAD compound and alkali metal are not combined prior to the combination of either (a) the DAD compound with the halogenated metal compound or halogenated metal complex compound or (b) the alkali metal with the halogenated metal compound or halogenated metal complex compound — S100

Purifying the mixture to obtain a liquid precursor composition containing a metal compound represented by Chemical Formula 1 — S200

FIG. 2

Mixing a halogenated metal compound represented by $MX_2$ or halogenated metal complex compound represented by $ZMX_2$ with a DAD compound — S50

Subsequently adding an alkali metal to form a mixture — S60

Reacting the mixture — S100

Purifying the mixture to obtain a liquid precursor composition containing a metal compound represented by Chemical Formula 1 — S200

FIG. 4B

| # | Time | Area | Height | Width | Area% | Symmetry |
|---|---|---|---|---|---|---|
| 1 | 4.002 | 253.1 | 79 | 0.0438 | 0.201 | 0.304 |
| 2 | 15.671 | 156.7 | 35.2 | 0.0679 | 0.125 | 0.732 |
| 3 | 16.037 | 19.6 | 4.9 | 0.0612 | 0.016 | 0.766 |
| 4 | 18.086 | 370.7 | 96.5 | 0.0576 | 0.295 | 0.565 |
| 5 | 19.774 | 23.7 | 3.9 | 0.0888 | 0.019 | 0.693 |
| 6 | 20.013 | 36.5 | 8.9 | 0.0638 | 0.029 | 0.755 |
| 7 | 21.9 | 44.5 | 4.7 | 0.134 | 0.035 | 2.714 |
| 8 | 22.05 | 43.4 | 7 | 0.0945 | 0.035 | 1.247 |
| 9 | 22.204 | 79.4 | 13 | 0.0906 | 0.063 | 1.634 |
| 10 | 22.36 | 253.6 | 41.4 | 0.0923 | 0.202 | 1.982 |
| 11 | 22.458 | 330.1 | 49.7 | 0.0982 | 0.263 | 0.877 |
| 12 | 22.598 | 818.8 | 14.4 | 0.0838 | 0.065 | 0.654 |
| 13 | 22.74 | 28.4 | 6 | 0.0748 | 0.023 | 0.966 |
| 14 | 23.22 | 21 | 3.5 | 0.0885 | 0.017 | 0.792 |
| 15 | 24.25 | 1209.4 | 70.8 | 0.2073 | 0.962 | 0.299 |
| 16 | 24.817 | 83.5 | 12.8 | 0.0955 | 0.066 | 1.729 |
| 17 | 25.649 | 121241.9 | 5914.1 | 0.2536 | 96.486 | 19.322 |
| 18 | 25.851 | 363 | 82.6 | 0.0625 | 0.289 | 1.396 |
| 19 | 25.923 | 445.7 | 95.5 | 0.0672 | 0.355 | 0.573 |
| 20 | 26.67 | 50 | 13.4 | 0.0581 | 0.04 | 1.029 |
| 21 | 26.772 | 186.4 | 50.8 | 0.0573 | 0.148 | 1.083 |
| 22 | 26.853 | 175.5 | 40.8 | 0.063 | 0.14 | 0.649 |
| 23 | 27.674 | 11.2 | 2.9 | 0.0597 | 0.009 | 1.141 |
| 24 | 28.383 | 57 | 11.4 | 0.0714 | 0.045 | 0.685 |
| 25 | 28.665 | 66.4 | 16.8 | 0.0622 | 0.053 | 0.758 |
| 26 | 29.668 | 24.4 | 5.9 | 0.0644 | 0.019 | 0.827 |

FIG. 6B

| # | Time | Area | Height | Width | Area% | Symmetry |
|---|---|---|---|---|---|---|
| 1 | 2.577 | 16.7 | 7.6 | 0.0305 | 0.012 | 0.267 |
| 2 | 2.665 | 8.4 | 3.2 | 0.0358 | 0.006 | 0.834 |
| 3 | 4.1 | 479.7 | 216.9 | 0.033 | 0.341 | 0.485 |
| 4 | 4.575 | 79.7 | 11.2 | 0.1033 | 0.057 | 0.279 |
| 5 | 7.071 | 65.4 | 6.3 | 0.1536 | 0.046 | 0.814 |
| 6 | 11.511 | 24 | 4.2 | 0.0819 | 0.017 | 0.526 |
| 7 | 18.372 | 168.5 | 52.5 | 0.0503 | 0.12 | 0.979 |
| 8 | 20.346 | 72.6 | 10.5 | 0.095 | 0.052 | 3.353 |
| 9 | 20.622 | 12.9 | 3.3 | 0.0592 | 0.009 | 0.692 |
| 10 | 21.289 | 7347.3 | 1379.1 | 0.0734 | 5.216 | 3.14 |
| 11 | 21.438 | 217.5 | 39.4 | 0.0788 | 0.154 | 0.804 |
| 12 | 21.938 | 93 | 25.9 | 0.0547 | 0.066 | 0.436 |
| 13 | 22.223 | 11.2 | 3 | 0.0576 | 0.008 | 0.741 |
| 14 | 23.226 | 24.8 | 6 | 0.0627 | 0.018 | 0.626 |
| 15 | 25.976 | 132237.5 | 6965.4 | 0.2295 | 93.879 | 17.652 |

*FIG. 7B*

| # | Time | Area | Height | Width | Area% | Symmetry |
|---|------|------|--------|-------|-------|----------|
| 1 | 4.17 | 1390.4 | 743.5 | 0.029 | 2.02 | 0.736 |
| 2 | 4.622 | 289 | 42.6 | 0.1007 | 0.42 | 0.286 |
| 3 | 5.139 | 241.6 | 80.8 | 0.0445 | 0.351 | 0.564 |
| 4 | 7.205 | 1137.7 | 110.9 | 0.1413 | 1.653 | 1.482 |
| 5 | 8.116 | 32.4 | 11.7 | 0.0426 | 0.047 | 0.666 |
| 6 | 10.714 | 26.8 | 7.8 | 0.0512 | 0.039 | 0.483 |
| 7 | 11.407 | 118.6 | 36.2 | 0.0502 | 0.172 | 0.449 |
| 8 | 16.091 | 114.3 | 18.6 | 0.0948 | 0.166 | 0.714 |
| 9 | 16.479 | 59.4 | 18.7 | 0.0507 | 0.086 | 0.99 |
| 10 | 17.53 | 9.7 | 2.8 | 0.0534 | 0.014 | 0.941 |
| 11 | 18.644 | 6171.1 | 949.2 | 0.0927 | 8.965 | 2.907 |
| 12 | 19.154 | 1594.4 | 442 | 0.5557 | 2.316 | 1.502 |
| 13 | 19.636 | 279.7 | 85 | 0.052 | 0.406 | 0.917 |
| 14 | 19.9 | 77.1 | 22.7 | 0.0508 | 0.112 | 1.451 |
| 15 | 19.992 | 566.8 | 160.2 | 0.0541 | 0.823 | 1.095 |
| 16 | 20.336 | 688.8 | 187.6 | 0.0572 | 1.001 | 0.992 |
| 17 | 20.474 | 486.7 | 134.4 | 0.0559 | 0.707 | 0.971 |
| 18 | 20.66 | 95.1 | 18.7 | 0.0721 | 0.138 | 0.594 |
| 19 | 21.015 | 186.4 | 51.5 | 0.5666 | 0.271 | 0.877 |
| 20 | 21.287 | 19.8 | 4 | 0.0699 | 0.029 | 0.488 |
| 21 | 21.573 | 939.5 | 139.2 | 0.0939 | 1.365 | 1.347 |
| 22 | 21.744 | 523.1 | 82.2 | 0.0974 | 0.76 | 1.416 |
| 23 | 23.176 | 47.7 | 12.1 | 0.0597 | 0.069 | 0.696 |
| 24 | 23.354 | 597.5 | 143.3 | 0.063 | 0.868 | 0.78 |
| 25 | 23.775 | 103.4 | 19 | 0.0796 | 0.15 | 0.433 |
| 26 | 24.208 | 542.9 | 7401 | 0.1087 | 0.789 | 0.698 |
| 27 | 25.84 | 36129.6 | 3058.6 | 0.1434 | 52.488 | 11.639 |
| 28 | 26.479 | 13340.6 | 1542.3 | 0.1097 | 19.381 | 4.665 |
| 29 | 27.163 | 1670.3 | 378.1 | 0.0667 | 2.427 | 2.037 |
| 30 | 27.27 | 1085.2 | 307.9 | 0.0539 | 1.577 | 1.324 |
| 31 | 27.916 | 127 | 32.4 | 0.0585 | 0.185 | 0.674 |
| 32 | 28.844 | 141.8 | 42.4 | 0.0526 | 0.206 | 1.019 |

FIG. 9B

| # | Time | Area | Height | Width | Area% | Symmetry |
|---|------|------|--------|-------|-------|----------|
| 1 | 4.068 | 2131.5 | 169.7 | 0.1577 | 1.702 | 0.112 |
| 2 | 26.192 | 123132.6 | 5507.1 | 0.3726 | 98.298 | 5.032 |

| # | Time | Area | Height | Width | Area% | Symmetry |
|---|------|------|--------|-------|-------|----------|
| 1 | 2.685 | 11.3 | 5.6 | 0.0316 | 0.01 | 0.594 |
| 2 | 4.328 | 259.6 | 103.1 | 0.039 | 0.232 | 0.578 |
| 3 | 4.753 | 33.1 | 13.4 | 0.0385 | 0.03 | 0.712 |
| 4 | 7.459 | 38.1 | 12.4 | 0.0469 | 0.034 | 0.82 |
| 5 | 10.913 | 34.8 | 11 | 0.0512 | 0.031 | 0.927 |
| 6 | 16.36 | 21.2 | 5.1 | 0.0628 | 0.019 | 1.322 |
| 7 | 17.819 | 904.3 | 257.6 | 0.057 | 0.809 | 1.206 |
| 8 | 18.228 | 82.6 | 25.6 | 0.052 | 0.074 | 1.038 |
| 9 | 18.78 | 115 | 22.2 | 0.0747 | 0.103 | 0.474 |
| 10 | 19.68 | 38.2 | 8.1 | 0.0713 | 0.034 | 0.809 |
| 11 | 19.804 | 21.8 | 5.4 | 0.0597 | 0.02 | 0.975 |
| 12 | 20.245 | 50.9 | 16.1 | 0.0496 | 0.046 | 0.981 |
| 13 | 20.615 | 9 | 2.5 | 0.0564 | 0.008 | 1.013 |
| 14 | 21.248 | 38.7 | 9.3 | 0.0613 | 0.035 | 0.797 |
| 15 | 21.602 | 310 | 14.4 | 0.1098 | 0.277 | 0.634 |
| 16 | 22.363 | 292.6 | 80.9 | 0.0566 | 0.262 | 1.068 |
| 17 | 22.834 | 92.5 | 21.4 | 0.0647 | 0.083 | 1.411 |
| 18 | 23.558 | 31.3 | 4 | 0.1039 | 0.028 | 1.381 |
| 19 | 24.364 | 26.2 | 4.8 | 0.084 | 0.023 | 0.86 |
| 20 | 24.559 | 24.8 | 4.7 | 0.0808 | 0.022 | 0.872 |
| 21 | 26.768 | 109404.8 | 6060.2 | 0.2186 | 97.813 | 13.37 |
| 22 | 27.95 | 10.6 | 3.1 | 0.0537 | 0.009 | 1.018 |

| # | Time | Area | Height | Width | Area% | Symmetry |
|---|------|------|--------|-------|-------|----------|
| 1 | 2.514 | 10.5 | 2.7 | 0.0581 | 0.009 | 0.464 |
| 2 | 4.005 | 787.2 | 241.2 | 0.0477 | 0.655 | 0.676 |
| 3 | 4.133 | 2578 | 307.5 | 0.1218 | 2.146 | 0.856 |
| 4 | 7.018 | 66.1 | 9.5 | 0.0969 | 0.055 | 0.415 |
| 5 | 26.241 | 115895 | 6222 | 0.2333 | 96.48 | 11.88 |
| 6 | 38.962 | 786.5 | 180.4 | 0.0685 | 0.655 | 16.81 |

| # | Time | Area | Height | Width | Area% | Symmetry |
|---|---|---|---|---|---|---|
| 1 | 2.58 | 96.4 | 42 | 0.0348 | 0.083 | 0.694 |
| 2 | 3.995 | 1614.1 | 478.1 | 0.049 | 1.387 | 0.394 |
| 3 | 6.994 | 79.9 | 17.2 | 0.0685 | 0.069 | 0.746 |
| 4 | 10.41 | 15.9 | 3.5 | 0.0669 | 0.014 | 0.607 |
| 5 | 18.26 | 13 | 4 | 0.0526 | 0.011 | 0.965 |
| 6 | 20.498 | 7.7 | 2.5 | 0.0503 | 0.007 | 1.011 |
| 7 | 20.661 | 16.3 | 4.3 | 0.0585 | 0.014 | 0.852 |
| 8 | 21.084 | 128.9 | 30.4 | 0.0671 | 0.111 | 1 |
| 9 | 21.276 | 39.1 | 5.9 | 0.0944 | 0.034 | 0.61 |
| 10 | 21.814 | 84.1 | 16.4 | 0.0806 | 0.072 | 0.991 |
| 11 | 22.109 | 16.7 | 4.2 | 0.0604 | 0.014 | 0.912 |
| 12 | 26.23 | 114108.5 | 6239.9 | 0.2277 | 98.077 | 11.48 |
| 13 | 26.692 | 16.9 | 2.4 | 0.095 | 0.015 | 0.922 |
| 14 | 27.399 | 15.2 | 4.7 | 0.0524 | 0.013 | 1.062 |
| 15 | 31.81 | 29.3 | 9 | 0.0523 | 0.025 | 0.979 |
| 16 | 32.07 | 7.1 | 2.1 | 0.0534 | 0.006 | 0.904 |
| 17 | 38.949 | 57 | 12.1 | 0.0726 | 0.049 | 1.542 |

| # | Time | Area | Height | Width | Area% | Symmetry |
|---|------|------|--------|-------|-------|----------|
| 1 | 2.695 | 5271.2 | 1297.1 | 0.073 | 3.574 | 0.553 |
| 2 | 2.969 | 9262 | 2934.6 | 0.0624 | 6.28 | 1.077 |
| 3 | 3.568 | 562.5 | 65.5 | 0.1257 | 0.381 | 0.759 |
| 4 | 4.102 | 225.3 | 32.2 | 0.1136 | 0.153 | 1.204 |
| 5 | 4.345 | 2754.4 | 660.7 | 0.0742 | 1.868 | 0.775 |
| 6 | 4.784 | 1870.8 | 158.6 | 0.1632 | 1.268 | 0.372 |
| 7 | 5.339 | 3035.6 | 555.7 | 0.0957 | 2.058 | 0.581 |
| 8 | 6.134 | 612.8 | 112.4 | 0.0956 | 0.416 | 0.909 |
| 9 | 7.565 | 22220.9 | 1620.3 | 0.1856 | 15.067 | 2.518 |
| 10 | 8.135 | 566.8 | 22.9 | 0.3213 | 0.384 | 0.93 |
| 11 | 8.839 | 935.3 | 56 | 0.2395 | 0.634 | 1.534 |
| 12 | 10.291 | 1494.5 | 136.1 | 0.1729 | 1.013 | 0.685 |
| 13 | 11.138 | 38931.5 | 3283.7 | 0.1831 | 26.397 | 1.916 |
| 14 | 11.616 | 1060.5 | 269.3 | 0.0779 | 0.719 | 1.194 |
| 15 | 11.921 | 1514 | 154 | 0.1467 | 1.027 | 0.449 |
| 16 | 12.759 | 642.5 | 87.8 | 0.1238 | 0.436 | 1.049 |
| 17 | 13.3 | 2701.3 | 271.5 | 0.1545 | 1.832 | 1.261 |
| 18 | 13.521 | 3775.2 | 620.1 | 0.0966 | 2.56 | 1.004 |
| 19 | 13.765 | 718.4 | 120.2 | 0.1017 | 0.487 | 0.911 |
| 20 | 14.112 | 531.6 | 45.9 | 0.1608 | 0.36 | 0.309 |
| 21 | 14.741 | 1371.4 | 213.1 | 0.1007 | 0.93 | 1.263 |
| 22 | 15.105 | 670.5 | 139.1 | 0.0818 | 0.455 | 0.607 |
| 23 | 16.351 | 704.3 | 155.1 | 0.085 | 0.478 | 0.799 |
| 24 | 16.704 | 233.9 | 33.4 | 0.1138 | 0.159 | 0.807 |
| 25 | 17.138 | 92.1 | 27.5 | 0.0711 | 0.062 | 1.172 |
| 26 | 18.208 | 1911.3 | 486.2 | 0.0779 | 1.296 | 0.923 |
| 27 | 18.784 | 2602.6 | 520.7 | 0.0903 | 1.765 | 1.046 |
| 28 | 19.379 | 817.9 | 204.4 | 0.0723 | 0.555 | 1.09 |
| 29 | 19.81 | 2694.9 | 394.3 | 0.1053 | 1.827 | 0.817 |
| 30 | 20.275 | 4905.6 | 788.7 | 0.1046 | 3.326 | 1.089 |
| 31 | 20.708 | 3094.1 | 252.9 | 0.1683 | 2.098 | 2.591 |
| 32 | 21.003 | 2229.1 | 167.7 | 0.1871 | 1.511 | 0.242 |
| 33 | 21.591 | 3741.2 | 279.5 | 0.1817 | 2.537 | 0.218 |
| 34 | 22.39 | 2767.4 | 265.7 | 0.1471 | 1.876 | 3.301 |
| 35 | 22.598 | 1190.2 | 162.5 | 0.1111 | 0.807 | 1.052 |
| 36 | 23.015 | 1695.5 | 172.8 | 0.1402 | 1.15 | 2.013 |
| 37 | 23.608 | 5065.2 | 305.8 | 0.2189 | 3.434 | 2.055 |
| 38 | 24.06 | 4091.1 | 631.3 | 0.1076 | 2.774 | 1.107 |
| 39 | 24.371 | 1890.8 | 146.9 | 0.1758 | 1.282 | 0.25 |
| 40 | 25.042 | 2116 | 220.9 | 0.1373 | 1.435 | 1.282 |
| 41 | 25.949 | 1995.1 | 356.8 | 0.0908 | 1.353 | 0.585 |
| 42 | 26.229 | 1943.2 | 386.1 | 0.0907 | 1.318 | 1.022 |
| 43 | 26.646 | 445.4 | 57.6 | 0.1159 | 0.302 | 0.459 |
| 44 | 27.877 | 416.3 | 81.2 | 0.0918 | 0.282 | 0.766 |
| 45 | 28.476 | 113.4 | 19 | 0.1017 | 0.077 | 0.976 |

FIG. 19B

| # | Time | Area | Height | Width | Area% | Symmetry |
|---|---|---|---|---|---|---|
| 1 | 2.662 | 3244 | 389.6 | 0.1227 | 2.143 | 0.127 |
| 2 | 4.299 | 1584.3 | 453.6 | 0.0664 | 1.049 | 0.723 |
| 3 | 4.724 | 3320.1 | 872.6 | 0.0764 | 2.193 | 0.742 |
| 4 | 5.29 | 1423.7 | 359.7 | 0.0718 | 0.941 | 0.969 |
| 5 | 6.085 | 504.5 | 73.3 | 0.1123 | 0.333 | 1.755 |
| 6 | 7.552 | 24416.5 | 2021.7 | 0.1729 | 16.131 | 2.218 |
| 7 | 8.876 | 947.2 | 73.2 | 0.1831 | 0.626 | 2.204 |
| 8 | 10.228 | 1471.9 | 286.3 | 0.092 | 0.972 | 0.953 |
| 9 | 10.925 | 4735.8 | 984.9 | 0.0817 | 3.129 | 1.005 |
| 10 | 11.548 | 398.7 | 79.1 | 0.0908 | 0.263 | 0.903 |
| 11 | 12.015 | 2630.1 | 112.6 | 0.3366 | 1.738 | 0.724 |
| 12 | 13.459 | 3311.5 | 473 | 0.1137 | 2.188 | 1.395 |
| 13 | 14.683 | 844.3 | 164.6 | 0.0918 | 0.558 | 1.063 |
| 14 | 15.749 | 579.1 | 134 | 0.076 | 0.383 | 1.023 |
| 15 | 16.287 | 337.7 | 83.6 | 0.0791 | 0.223 | 0.98 |
| 16 | 17.732 | 120.5 | 24.9 | 0.0884 | 0.08 | 1.029 |
| 17 | 18.161 | 2339.1 | 607.7 | 0.0705 | 1.545 | 0.986 |
| 18 | 18.734 | 2434.3 | 538.6 | 0.0783 | 1.608 | 1.028 |
| 19 | 19.327 | 2536.3 | 539.5 | 0.081 | 1.693 | 1.96 |
| 20 | 19.741 | 612.3 | 65.1 | 0.1354 | 0.405 | 0.431 |

| # | Time | Area | Height | Width | Area% | Symmetry |
|---|---|---|---|---|---|---|
| 21 | 20.185 | 2712.6 | 664.5 | 0.0732 | 1.792 | 1.009 |
| 22 | 20.657 | 1745.6 | 335.1 | 0.0864 | 1.153 | 0.557 |
| 23 | 21.817 | 1599.7 | 229.6 | 0.1197 | 1.057 | 1.185 |
| 24 | 23.537 | 572.3 | 54.6 | 0.1543 | 0.378 | 0.821 |
| 25 | 25.634 | 36218.6 | 502.2 | 0.9757 | 23.928 | 3.169 |
| 26 | 26.162 | 36938.4 | 2083.9 | 0.2388 | 24.403 | 0.329 |
| 27 | 26.853 | 7288.4 | 90.5 | 0.254 | 1.204 | 1.086 |
| 28 | 27.199 | 1715.5 | 908.1 | 0.0906 | 1.133 | 0.948 |
| 29 | 27.517 | 1607.7 | 194.9 | 0.1218 | 1.062 | 0.337 |
| 30 | 27.976 | 2084 | 401.7 | 0.0861 | 1.377 | 0.554 |
| 31 | 28.435 | 2454.3 | 505.7 | 0.0886 | 1.621 | 0.929 |
| 32 | 29.286 | 2317.2 | 153.4 | 0.2274 | 1.531 | 0.964 |
| 33 | 31.49 | 223.4 | 30.1 | 0.1249 | 0.148 | 0.962 |
| 34 | 31.806 | 259.6 | 56.2 | 0.0795 | 0.172 | 0.914 |
| 35 | 31.186 | 637.2 | 74.8 | 0.1378 | 0.421 | 0.929 |
| 36 | 33.657 | 638.3 | 55.4 | 0.1601 | 0.422 | 0.661 |

LIQUID PRECURSOR COMPOSITIONS, PREPARATION METHODS THEREOF, AND METHODS FOR FORMING LAYER USING THE COMPOSITION

CROSS-REFERENCE TO RELATED APPLICATIONS

This application is a continuation of PCT Application No. PCT/KR2015/005945, filed Jun. 12, 2015, which claims priority to Korean Patent Application Number 10-2014-0072274, filed Jun. 13, 2014, both of which are hereby incorporated by reference in their entirety.

TECHNICAL FIELD

The present disclosure relates to liquid precursor compositions, preparation methods of the liquid precursor compositions, and methods for forming layers using the liquid precursor composition.

BACKGROUND

Chemical vapor deposition (CVD) and atomic layer deposition (ALD) provide methods for forming metal-containing layers on target substrates by supplying gases containing metal compounds to a deposition chamber or other deposition equipment. They have been widely used to manufacture electronic devices, semiconductor devices, display devices, and so on. Particularly, the semiconductor industry needs novel metal compounds and/or compositions for depositing metal-containing layers, such as metal layers, metal silicide layers, metal oxide layers, and metal nitride layers with desirable properties.

Amidinate compounds of nickel or cobalt have been used as precursors for ALD [B. S. Lim, A. Rahtu, J. S. Park, and R. G. Gordon, Inorganic Chemistry, 42, 7951 (2003)]. However, compositions having a high content of the amidinate compounds are in a solid state at room temperature and thus are not suitable for volume production of semiconductor devices using CVD or ALD.

Carbonyl compounds of cobalt or nickel are also in solid state at room temperature and thus not suitable for volume production of semiconductor devices using CVD or ALD. A few liquid cobalt precursors such as dicobalt hexacarbonyl tert-butylacetylene (CCTBA) or cyclopentadielycobalt dicarbonyl [$(C_5H_5)Co(CO)_2$] are available commercially; however, they have to be used at a relatively low deposition temperature because they are not thermally stable. Few liquid nickel precursors are known and none is available commercially. And thus the semiconductor industry needs a liquid precursor composition for vapor deposition of cobalt- or nickel-containing layers.

SUMMARY

In view of the foregoing, one purpose of the present disclosure is to provide liquid precursor compositions that can be used, for example, for deposition, methods for preparing the liquid precursor compositions, and methods for forming metal or metal compound-containing layers using the liquid precursor compositions.

However, the embodiments of the present disclosure are not limited to providing any particular advantages. Although not described herein, other advantages associated with the compositions, processes and methods of the present disclosure and uses thereof can be clearly understood by those skilled in the art from the following descriptions.

In a first aspect of the present disclosure, liquid precursor compositions are provided, including: metal compounds represented by the following Chemical Formula 1:

$M(DAD)_2$;  <Chemical Formula 1> wherein in the Chemical Formula 1,

M denotes Co or Ni, and

DAD denotes a diazadiene ligand compound represented by $R^1NC(R^3)C(R^4)NR^2$, wherein each of $R^1$ to $R^4$ includes independently H; or a linear or branched $C_{1-5}$ alkyl group.

In a second aspect of the present disclosure, methods are provided for preparing liquid precursor compositions in accordance with the first aspect of the present disclosure. In some embodiments, the methods comprise reacting a mixture containing a halogenated metal compound represented by $MX_2$ or a halogenated metal complex compound represented by $ZMX_2$ (where M is Co or Ni; X is a halogen; and Z is one or more neutral ligands), a diazadiene ligand compound represented by DAD, and an alkali metal in a solvent. Z may be any neutral ligand(s) commonly known in the art, which preferably does not interfere with the synthesis of $M(DAD)_2$. In some embodiments, Z may be at least one neutral ligand selected from the group consisting of 1,2-dimethoxyethane (DME), tetrahydrofuran (THF), 2-methoxyethyl ether, ammonia ($NH_3$), pyridine, N,N,N',N'-tetramethyl-1,2-ethylenediamine, tricyclohexylphosphine, triphenylphosphine, 1,2-Bis(diphenylphosphino)ethane, and 1,3-Bis(diphenylphosphino)propane. In some embodiments, X may be Cl, Br or I.

In some embodiments in forming the mixture, the DAD compound and alkali metal are not combined prior to the combination of either (a) the DAD compound with the halogenated metal compound or halogenated metal complex compound or (b) the alkali metal with the halogenated metal compound or halogenated metal complex compound. The reaction may be followed by purification to obtain a composition containing a metal compound represented by the following Chemical Formula 1:

$M(DAD)_2$;  <Chemical Formula 1> wherein,

M denotes Co or Ni, and

DAD denotes diazadiene ligand compound represented by $R^1NC(R^3)C(R^4)NR^2$, wherein each of $R^1$ to $R^4$ includes independently H; or a linear or branched alkyl group of $C_{1-5}$.

In some exemplary embodiments of the present disclosure, the mixture may be obtained by mixing the halogenated metal compound or halogenated metal complex compound with the diazadiene ligand compound DAD, and then subsequently adding the alkali metal.

In some exemplary embodiments of the present disclosure, the mixture may be obtained by mixing the halogenated metal compound or halogenated metal complex compound with the alkali metal, and then adding the diazadiene ligand compound DAD.

In a third aspect of the present disclosure, methods are provided for forming a layer, such as by vapor deposition, for example by CVD or ALD. In some embodiments, the methods comprise depositing a layer containing a metal or metal compound using a liquid precursor composition in accordance with the first aspect of the present disclosure as represented by the following Chemical Formula 1:

$M(DAD)_2$;  <Chemical Formula 1> wherein in the Chemical Formula 1,
M denotes Co or Ni, and
DAD denotes a diazadiene ligand compound represented by $R^1NC(R^3)C(R^4)NR^2$, wherein each of $R^1$ to $R^4$ includes independently H; or a linear or branched $C_{1-5}$ alkyl group.

In some embodiments of each of the aspects of the invention, the metal compound of Chemical Formula 1 is at least about 80% or more, about 85% or more, about 90% or more, or 95% or more of the liquid precursor composition. Herein, the content may be determined by, for example, chromatography. In some embodiments, the chromatography may be a gas chromatography, but is not limited thereto.

In some embodiments, the purity of the liquid precursor composition may be at least about 80% or more, about 85% or more, about 90% or more, or 95% or more. That is, in some embodiments, impurities (components other than the metal compound of Chemical Formula 1) may be about 20% or less, about 15% or less, about 10% or less or even about 5% or less. The purity may also be determined by, for example, chromatography. In some embodiments, the chromatography may be a gas chromatography, but is not limited thereto.

Effect of Embodiments

A liquid precursor composition in accordance with some exemplary embodiments of the present disclosure, or a liquid source material prepared from the liquid precursor composition, is advantageous in forming layers containing a metal or metal compound, particularly nickel or cobalt. For example, the liquid precursor composition may be used to deposit a cobalt or nickel metallic film. In some embodiments, the metallic film may comprise at least about 80 at % nickel or cobalt. Further, liquid precursor compositions in accordance with exemplary embodiments of the present disclosure may also be used in forming layers of a cobalt compound or a nickel compound, such as a cobalt silicide layer, a cobalt oxide layer, a cobalt nitride layer, a nickel oxide layer, a nickel nitride layer, a nickel silicide layer, etc.

In some embodiments, the liquid precursor compositions in accordance with exemplary embodiments of the present disclosure have a high purity. In some embodiments, the use of high-purity compositions can increase the reproducibility of a volume production process of semiconductor devices, which is advantageous in manufacturing semiconductor devices with uniform properties. Further, the use of a high-purity composition as disclosed herein can avoid other problems associated with the use of low-purity compositions. For example, when a low-purity precursor composition containing a significant amount of impurities is used, semiconductor devices may not have uniform properties in each batch due to low reproducibility of a semiconductor device manufacturing process and a lot of defective semiconductor devices may be produced. In some embodiments such problems may be avoided using the compositions provided herein.

BRIEF DESCRIPTION OF THE DRAWINGS

FIG. 1 is a flow chart showing a method for preparing a liquid precursor in accordance with an illustrative embodiment of the present disclosure.

FIG. 2 is a flow chart showing a method for preparing a liquid precursor in accordance with an illustrative embodiment of the present disclosure.

FIG. 4A and FIG. 4B show a gas chromatography-flame ionization detector (GC-FID) analysis results of a liquid precursor composition containing $Co(^iPr-DAD)_2$ which was prepared in accordance with Example 1.

FIG. 6A and FIG. 6B show a GC-FID analysis results of a liquid precursor composition which containing $Co(^iPr-DAD)_2$ which was prepared in accordance with Example 2.

FIG. 7A and FIG. 7B show a GC-FID analysis results of a liquid precursor composition which containing $Co(^iPr-DAD)_2$ which was prepared in accordance with Comparative Example 1.

FIG. 9A and FIG. 9B show a GC-FID analysis results of a liquid precursor composition containing $Ni(^iPr-DAD)_2$ which was prepared in accordance with Example 3.

FIG. 11A and FIG. 11B show a GC-FID analysis results of a liquid precursor composition containing $Ni(^iPr-DAD)_2$ which was prepared in accordance with Example 4.

FIG. 13A and FIG. 13B show a GC-FID analysis results of a liquid precursor composition containing $Ni(^iPr-DAD)_2$ which was prepared in accordance with Example 5.

FIG. 15A and FIG. 15B show a GC-FID analysis results of a liquid precursor composition containing $Ni(^iPr-DAD)_2$ which was prepared in accordance with Example 6.

FIG. 17A and FIG. 17B show a GC-FID analysis results of a liquid precursor composition containing $Ni(^iPr-DAD)_2$ which was prepared in accordance with Comparative Example 2.

FIG. 19A and FIG. 19B show a GC-FID analysis results of a liquid precursor composition containing $Ni(^iPr-DAD)_2$ which was prepared in accordance with Comparative Example 3.

DETAILED DESCRIPTION

Figure 3:
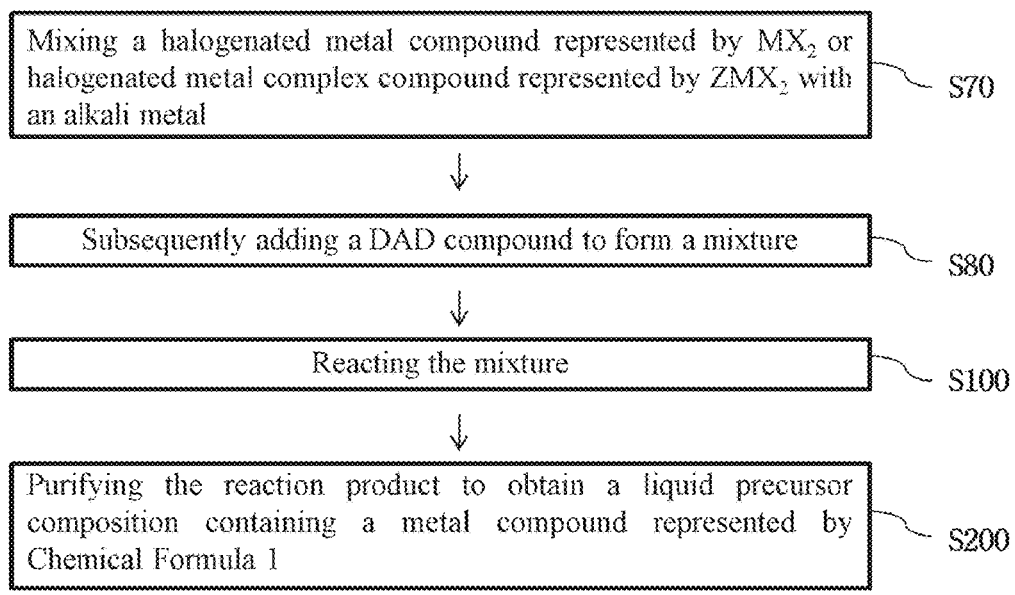
FIG. 3 is a flow chart showing a method for preparing a liquid precursor in accordance with an illustrative embodiment of the present disclosure.

Hereinafter, embodiments of the present disclosure will be described in detail, with reference where appropriate to the accompanying drawings, so that the present disclosure may be readily implemented by those skilled in the art.

However, it is to be noted that the present disclosure is not limited to the embodiments disclosed herein but can be embodied in various other ways.

Through the whole document of the present disclosure, the term "comprises or includes" and/or "comprising or including" used in the document means that one or more other components, steps, operation and/or the existence or addition of elements are not excluded in addition to the described components, steps, operation and/or elements unless context dictates otherwise.

The term "about or approximately" or "substantially" is intended to have meanings close to numerical values or ranges specified with an allowable error. Through the whole document, the term "step of" does not mean "step for".

Throughout the present disclosure, the term "combinations of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Throughout the present disclosure, the term "A and/or B" means "A or B, or A and B".

Throughout the present disclosure, the term "alkyl" may include a linear or branched alkyl group having carbon atoms in a number ranging from 1 to 5. By way of example, the alkyl group may be methyl group, ethyl group, n-propyl group, isopropyl group, n-butyl group, t-butyl group, isobutyl group, sec-butyl group, etc., but may not be limited thereto.

Throughout the present disclosure, the term "halogenated metal compound" refers to a halogenated metal compound represented by $MX_2$ or a halogenated metal complex compound represented by $ZMX_2$, where X is a halogen and Z is one or more neutral ligands such as DME, THF, 2-methoxyethyl ether, ammonia, pyridine, N,N,N',N'-tetramethyl-1,2-ethylenediamine, tricyclohexylphosphine, triphenylphosphine, 1,2-Bis(diphenylphosphino)ethane, or 1,3-Bis(diphenylphosphino)propane. In some embodiments, Z may be any other neutral ligand commonly known in the art. However, the neutral ligand preferably does not interfere the synthesis of $M(DAD)_2$.

The halogenated metal complex compound represented by $ZMX_2$ may include a complex compound or its derivative, such as $(DME)NiBr_2$, in which a neutral ligand such as 1,2-dimethoxyethane (DME) is combined with a halogenated metal compound. In some embodiments, it may be a complex compound or its derivative combined with a neutral ligand such as tetrahydrofuran (THF) or 2-methoxyethyl ether. In some embodiments, it may be a complex compound or its derivative, such as $Ni(NH_3)_6Br_2$, in which neutral ligands, such as six ammonias, are combined with a halogenated metal compound.

Hereinafter, exemplary embodiments of the present disclosure will be described in detail, but the present disclosure is not intended to be limited thereto.

Throughout the present disclosure, in order to measure elements or contents of the liquid precursor compositions, any and all conventionally known methods can be used. For example, in some embodiments, a known chromatography method may be used to separate components and determine contents, constituents, or purity of the components. According to the chromatography, the content or composition, of a liquid precursor composition or other composition with respect to a specific component can be determined on the basis of a ratio of an area of a peak for the specific component relative to the sum of areas of all the detected peaks. The purity of the liquid precursor can be also be determined on the basis of a ratio of an area of a peak for the specific compound of interest, typically $M(DAD)_2$, relative to all other components. The content can be presented as the percentage (%) of the area of the peak for the specific component of interest (typically $M(DAD)_2$) relative to the sum of the areas of all detected peaks. Similarly, purity can be presented as the % of the specific component of interest relative to the total components or as the % of components (impurities) other than the component of interest (typically $M(DAD)_2$) relative to the total components. Commercial chromatography devices can be used and will generally output an analysis result showing contents, constituents, or purity expressed by % together with chromatograms. In some embodiments, a gas chromatography (GC) device using a flame ionization detector (FID) can be used, as has been widely used in the art to measure contents, compositions, or purity. However, the present disclosure is not limited thereto. As discussed below, in some embodiments, a liquid precursor composition may be combined with one or more additional components, such as diluents, to form, for example, a liquid source material. Thus, the content and purity of the liquid precursor composition, with respect to the compound of interest (typically $M(DAD)_2$), may differ from the content and purity of a liquid source material.

In a first aspect of the present disclosure, liquid precursor compositions are provided. In some embodiments of the present disclosure, the liquid precursor composition may be used for depositing a layer containing a metal, such as Ni or Co, or metal compound, such as a Ni- or Co-containing compound. In some embodiments of the present disclosure, the liquid precursor compositions may be used for depositing a metal-containing layer, such as a Ni- or Co-containing layer, by a vapor deposition process. For example, the liquid precursor compositions may be used in metal organic chemical vapor deposition (MOCVD) or atomic layer deposition (ALD) processes. The type of deposition process is not limited thereto, and other deposition process in which the liquid precursor compositions may be used will be apparent to the skilled artisan.

In some embodiments, the liquid precursor compositions comprise a metal compound represented by the following Chemical Formula 1:

M(DAD)$_2$;  <Chemical Formula 1> wherein in the Chemical Formula 1,

M denotes Co or Ni, and

DAD denotes a diazadiene ligand compound represented by R$^1$NC(R$^3$)C(R$^4$)NR$^2$, wherein each of R$^1$ to R$^4$ may be independently H, or a linear or branched C$_{1-5}$ alkyl group.

The diazadiene ligand as a neutral ligand may be present in the form of a compound, and may be abbreviated throughout the present disclosure. For example, HNCHCHNH may be abbreviated as H-DAD; MeNCHCHNMe may be abbreviated as Me-DAD; EtNCHCHNEt may be abbreviated as Et-DAD; $^n$PrNCHCHN$^n$Pr may be abbreviated as $^n$Pr-DAD; $^i$PrNCHCHN$^i$Pr may be abbreviated as $^i$Pr-DAD; $^n$BuNCHCHN$^n$Bu may be abbreviated as $^n$Bu-DAD; $^t$BuNCHCHN$^t$Bu may be abbreviated as $^t$Bu-DAD; $^{sec}$BuNCHCHN$^{sec}$Bu may be abbreviated as $^{sec}$Bu-DAD. Herein, Me represents a methyl group, Et represents an ethyl group, $^n$Pr represents n-propyl group, $^i$Pr represents isopropyl group, $^n$Bu represents n-butyl group, $^t$Bu represents tert-butyl group, and $^{sec}$Bu represents a sec-butyl group.

In some embodiments of the present disclosure, the diazadiene ligand may include one in which either independently or both of R$^1$ and R$^2$ may be an isopropyl group or tert-butyl group, and both of R$^3$ and R$^4$ may be H, but is not intended to be limited thereto. By way of example, the diazadiene ligand may include $^i$Pr-DAD or $^t$Bu-DAD, but is not intended to be limited thereto.

By way of example, in some embodiments, a liquid precursor composition may comprise Co($^i$PrNCHCHN$^i$Pr)$_2$ [abbreviation: Co($^i$Pr-DAD)$_2$], which may have a molecular weight of about 339 g/mol.

In some embodiments, a liquid precursor composition may comprise compound Ni($^i$PrNCHCHN$^i$Pr)$_2$ [abbreviation: Ni($^i$Pr-DAD)$_2$], which may have a molecular weight of about 339 g/mol.

In some embodiments of the present disclosure, the metal compound of Chemical Formula 1 is at least about 80% or more, about 85% or more, about 90% or more, or 95% or more of the liquid precursor composition. Herein, the content may be determined by, for example, chromatography as mentioned above. In some embodiments, the chromatography may be a gas chromatography, but is not limited thereto.

In some embodiments of the present disclosure, a liquid precursor composition may consist substantially or essentially of the metal compound of Chemical Formula 1.

In some embodiments, the purity of the liquid precursor composition with respect to the metal compound of Chemical Formula 1 may be at least about 80% or more, about 85% or more, about 90% or more, or 95% or more. That is, impurities (components other than the metal compound of Chemical Formula 1) are about 20% or less, about 15% or less, about 10% or less or even about 5% or less. Herein, the purity may be determined by, for example, chromatography. In some embodiments, the chromatography may be a gas chromatography, but is not limited thereto.

In some embodiments, the liquid precursor composition may be diluted or otherwise mixed with one or more additional components to form a liquid source material. For example, the liquid precursor composition may be mixed with one or more inert ingredients, such as an inert diluent, for storage or use. A liquid source material comprising the liquid precursor composition may be used in some embodiments described herein rather than using the liquid precursor composition directly. In addition, it is noted that the composition and purity of the liquid precursor composition, with respect to the M(DAD)$_2$ compound, may differ from the composition and purity of a liquid source material due to the presence of additional compounds in the liquid precursor composition. When the composition and/or purity of a liquid precursor composition is provided herein, the composition and purity is given relative to the liquid precursor composition itself and does not take into account any additional ingredients with which the liquid precursor composition may be combined, such as diluents.

In some embodiments of the present disclosure, at least about 80% or more, about 85% or more, about 90% or more, or 95% or more of the liquid precursor composition is the compound Co($^i$PrNCHCHN$^i$Pr)$_2$. The content of the liquid precursor composition may be determined by, for example, chromatography. In some embodiments, the chromatography may be a gas chromatography, but is not limited thereto.

In some embodiments, the purity of a liquid precursor composition comprising Co($^i$PrNCHCHN$^i$Pr)$_2$ may be about 80% or more, about 85% or more, about 90% or more, or 95% or more, but is not limited thereto. That is, impurities (components other than the metal compound Co($^i$PrNCHCHN$^i$Pr)$_2$) may be about 20% or less, about 15% or less, about 10% or less or even about 5% or less. Herein, the purity may be determined by, for example, chromatography. In some embodiments, the chromatography may be a gas chromatography, but is not limited thereto.

In some embodiments of the present disclosure, at least about 80% or more, about 85% or more, about 90% or more, or 95% or more of a liquid precursor composition is the compound Ni($^i$PrNCHCHN$^i$Pr)$_2$. The content of the liquid precursor composition may be determined by, for example, chromatography. In some embodiments, the chromatography may be gas chromatography, but is not limited thereto.

In some embodiments, the purity of the liquid precursor composition comprising Ni($^i$PrNCHCHN$^i$Pr)$_2$ may be about 80% or more, about 85% or more, about 90% or more, or 95% or more, but is not limited thereto. That is, impurities (components other than the metal compound Ni($^i$PrNCHCHN$^i$Pr)$_2$) are about 20% or less, about 15% or less, about 10% or less or even about 5% or less. Herein, the purity may be determined by, for example, chromatography. In some embodiments, the chromatography may be a gas chromatography, but is not limited thereto.

In some embodiments of the present disclosure, a liquid precursor composition may consist substantially or essentially of the metal compound represented by Co($^i$PrNCHCHN$^i$Pr)$_2$. In some embodiments, the liquid precursor composition may have a molecular weight of about 339 g/mol.

In some embodiments of the present disclosure, the liquid precursor composition may consist substantially or essentially of the metal compound represented by Ni($^i$PrNCHCHN$^i$Pr)$_2$. In some embodiments, the liquid precursor composition may have a molecular weight of about 339 g/mol.

Liquid Precursor Preparation

In a second aspect of the present disclosure, methods for preparing a liquid precursor composition in accordance with the first aspect of the present disclosure are provided. In some embodiments, as illustrated in FIG. 1, the methods comprise: reacting a mixture containing a halogenated metal compound represented by MX$_2$ or a halogenated metal complex compound represented by ZMX$_2$ (where M is Ni or Co; X is a halogen; and Z is one or more neutral ligands), a diazadiene ligand compound DAD, and an alkali metal in a solvent (S100), followed by purification (S200). In some embodiments, Z may be selected from the group consisting of DME, THF, 2-methoxyethyl ether, ammonia, pyridine, N,N,N',N'-tetramethyl-1,2-ethylenediamine, tricyclohexylphosphine, triphenylphosphine, 1,2-Bis(diphenylphosphino) ethane, and 1,3-Bis(diphenylphosphino)propane. In some embodiments, Z may be any neutral ligand commonly known in the art, preferably one that does not interfere the synthesis of $M(DAD)_2$.

As illustrated in several embodiments discussed below, and in FIGS. 1 to 3, In some embodiments, the DAD and alkali metal are not combined prior to the combination of one or both of the DAD and/or alkali metal with the halogenated metal compound or halogenated metal complex compound.

A liquid precursor composition containing a metal compound represented by the following Chemical Formula 1 is obtained:

$$M(DAD)_2; \qquad \text{<Chemical Formula 1>}$$

wherein,

M denotes Co or Ni, and

DAD denotes a diazadiene ligand compound represented by $R^1NC(R^3)C(R^4)NR^2$, wherein each of $R^1$ to $R^4$ includes independently H; or a linear or branched alkyl group of $C_{1-5}$.

In some embodiments of the present disclosure, at least about 80% or more, about 85% or more, about 90% or more, or 95% or more of the liquid precursor composition obtained by the preparation methods is a metal compound of Chemical Formula 1.

The preparation process may produce a liquid precursor composition that includes some amount of components other than the metal compound of Chemical Formula 1. In some embodiments, the liquid precursor composition obtained by the preparation methods may have a purity with respect to Chemical Formula 1 of about 80% or more, about 85% or more, about 90% or more, or 95% or more, but may not be limited thereto. That is, impurities (components other than the metal compound of Chemical Formula 1) are about 20% or less, about 15% or less, about 10% or less or even about 5% or less.

In some embodiments, the content and/or purity may be determined by, for example, chromatography. In some embodiments, the chromatography may be gas chromatography, but is not limited thereto.

In some embodiments of the present disclosure, the purification may be performed by a single or multiple step(s) of reduced-pressure distillation, but the purification is not limited thereto and may be carried out by other methods known in the art. In some embodiments, one, two or three reduced-pressure distillation steps are carried out.

In some embodiments of the present disclosure, the liquid precursor compositions obtained by the preparation methods may be used for depositing a metal-containing layer by vapor deposition, such as by organic metal chemical vapor deposition (MOCVD) or atomic layer deposition (ALD), but not limited thereto.

In some embodiments of the present disclosure, at least about 80% or more, about 85% or more, about 90% or more, or 95% or more of the liquid precursor composition obtained by the preparation methods may be the compound Co($^i$PrNCHCHN$^i$Pr)$_2$. The content may be determined by, for example, using chromatography. In some embodiments, the chromatography may be gas chromatography, but is not limited thereto.

In some embodiments of the present disclosure, the purity of the liquid precursor composition with respect to the metal compound Co($^i$PrNCHCHN$^i$Pr)$_2$ and obtained by the preparation methods may be about 80% or more, about 85% or more, about 90% or more, or 95% or more, but is not limited thereto. That is, impurities (components other than the metal compound Co($^i$PrNCHCHN$^i$Pr)$_2$) may be about 20% or less, about 15% or less, about 10% or less or even about 5% or less in some embodiments. The purity may be determined by, for example, using chromatography. In some embodiments, the chromatography may be gas chromatography, but is not limited thereto.

In some embodiments, the preparation methods are used to produce Co($^i$PrNCHCHN$^i$Pr)$_2$ [abbreviation: Co($^i$PrDAD)$_2$], which may have a molecular weight of about 339 g/mol.

In an example embodiment of the present disclosure, at least about 80% or more, about 85% or more, about 90% or more, or 95% or more of the liquid precursor composition obtained by the preparation methods may be the metal compound represented by Ni($^i$PrNCHCHN$^i$Pr)$_2$. The content may be determined by, for example, using chromatography. In some embodiments, the chromatography may be gas chromatography, but is not limited thereto.

In some embodiments of the present disclosure, the purity of the liquid precursor composition with respect to the metal compound Ni($^i$PrNCHCHN$^i$Pr)$_2$ and obtained by the preparation methods may be about 80% or more, about 85% or more, about 90% or more, or 95% or more, but is not limited thereto. That is, impurities (components other than the metal compound Ni($^i$PrNCHCHN$^i$Pr)$_2$) are about 20% or less, about 15% or less, about 10% or less or even about 5% or less. The purity may be determined by, for example, using chromatography. In some embodiments, the chromatography may be gas chromatography, but is not limited thereto.

In some embodiments, the preparation methods are used to produce Ni($^i$PrNCHCHN$^i$Pr)$_2$ [abbreviation: Ni($^i$PrDAD)$_2$], which may have a molecular weight of about 339 g/mol.

In some embodiments of the present disclosure, the liquid precursor composition formed by the preparation methods may consist substantially or essentially of the metal compound represented by Co($^i$PrNCHCHN$^i$Pr)$_2$.

In some embodiments of the present disclosure, the liquid precursor composition formed by the preparation methods may consist substantially or essentially of the metal compound represented by Ni($^i$PrNCHCHN$^i$Pr)$_2$.

As mentioned above, in some embodiments, such as that disclosed in FIG. 1, a mixture is formed containing one equivalent of a halogenated metal compound represented by $MX_2$ or a halogenated metal complex compound represented by $ZMX_2$ (where M is Ni or Co; X is a halogen; and Z is one or more neutral ligand(s)), about two equivalents of a diazadiene ligand compound DAD, and about two equivalents of an alkali metal in a solvent. The mixture is reacted to form a reaction product (S100), which can then be purified as described above to form a liquid precursor composition comprising a metal compound represented by Chemical Formula 1 ($M(DAD)_2$) (S200). In some embodiments, the metal compound makes up at least about 80%, about 85%, about 90%, about 95% or more of the liquid precursor composition.

It was determined that it can be advantageous if the dissolution reaction of the alkali metal occurs at a final step in the mixing of the reactants. Thus, in some embodiments, the DAD compound and the alkali metal are not reacted together initially. For example, in some embodiments, in forming the mixture the DAD compound and alkali metal are not combined prior to the combination of either (a) the DAD compound with the halogenated metal compound or halogenated metal complex compound or (b) the alkali metal with the halogenated metal compound or halogenated metal complex compound.

In some embodiments, for example as disclosed in FIG. 2, the mixture is obtained by mixing the halogenated metal compound represented by $MX_2$ or halogenated metal complex compound represented by $ZMX_2$ with the diazadiene ligand compound DAD (S50), and then subsequently adding the alkali metal (S60). In this way, the alkali metal is not dissolved but remains in a solid state until it is added to the mixture. In some embodiments, the alkali metal may be dissolved while adding the alkali metal; or the alkali metal may be dissolved after completely adding the alkali metal. For one example, the alkali metal may be added at a very low temperature at which no dissolution of the alkali metal occurs (S60), and then subsequently the mixture warms up to be reacted while the dissolution of the alkali metal occurs (S100). For another example, the alkali metal may be added at a temperature at which the dissolution of the alkali metal occurs and thus the reaction of the mixture occurs while adding the alkali metal, which means that S60 and S100 in FIG. 2 occur concurrently.

In some embodiments, for example as disclosed in FIG. 3, the mixture may be obtained by mixing the halogenated metal compound represented by $MX_2$ or halogenated metal complex compound represented by $ZMX_2$ with the alkali metal (S70), and then subsequently adding the diazadiene ligand compound DAD (S80). In this way, during the step of mixing the halogenated metal compound represented by $MX_2$ or halogenated metal complex compound represented by $ZMX_2$ with the alkali metal, the alkali metal is not dissolved but remains in a solid state. Then, in the step of adding the diazadiene ligand compound DAD, a dissolution reaction of the alkali metal occurs (S100). The dissolution of the alkali metal may occur while adding the DAD compound; or it may occur after completely adding the DAD compound. For one example, the DAD compound may be added at a very low temperature at which no dissolution of the alkali metal occurs (S80), and then subsequently the mixture warms up to be reacted while the dissolution of the alkali metal occurs (S100). For another example, the DAD compound may be added at a temperature at which the dissolution of the alkali metal occurs and thus the reaction of the mixture occurs while adding the alkali metal, which means that S80 and S100 in FIG. 3 occur concurrently.

A composition which is prepared by mixing two equivalents of an alkali metal with two equivalents of a diazadiene ligand compound DAD to completely dissolve the alkali metal, and then, subsequently adding one equivalent of the halogenated metal compound represented by $MX_2$ or halogenated metal complex compound represented by $ZMX_2$, is greatly different from a composition prepared in accordance with the exemplary embodiments disclosed above, both in terms of gas chromatography analysis results and deposition results of a layer containing a metal or metal compound by CVD or ALD.

According to the preparation method in which two equivalents of the alkali metal and two equivalents of the diazadiene ligand compound DAD are mixed first to completely dissolve the alkali metal, and then one equivalent of the halogenated metal compound represented by $MX_2$ or halogenated metal complex compound represented by $ZMX_2$ is added, a liquid precursor composition wherein at least about 80% or more of the liquid precursor composition is a metal compound represented by the Chemical Formula 1 is not produced. In addition, such a process does not produce a composition which has a purity of at least about 80%.

In some embodiments, a preparation process for preparing a liquid precursor composition comprising a compound of Chemical Formula 1 comprises a reaction scheme as represented by the following Reaction Formula 1 or 2. In particular, in some embodiments as illustrated in Reaction Formula 1, a mixture is formed of a diazadiene ligand DAD represented by the following Chemical Formula 2 and the halogenated metal compound represented by $MX_2$ or halogenated metal complex compound represented by $ZMX_2$. Subsequently, an alkali metal (M') is added to the mixture to allow a reaction therebetween and the production of the $M(DAD)_2$ product. A single or multiple step(s) of reduced-pressure distillation may then be carried out for purification. For example, one, two or three reduced-pressure distillations may be carried out.

In some embodiments, as illustrated in Reaction Formula 2, a mixture of a halogenated metal compound represented by $MX_2$ or halogenated metal complex compound represented by $ZMX_2$ and an alkali metal (M') diazadiene is prepared. The ligand DAD represented by the following Chemical Formula 2 is added to the mixture to allow reaction there between, which produces $M(DAD)_2$. A single or multiple step(s) of reduced-pressure distillation can then be performed for purification. For example, one, two or three reduced-pressure distillations may be carried out.

[Chemical Formula 2]

[Reaction Formula 1]

[Reaction Formula 2]

wherein in the above formulas,

M denotes Co or Ni; and DAD denotes a diazadiene ligand compound represented by $R^1NC(R^3)C(R^4)NR^2$, wherein each of $R^1$ to $R^4$ includes independently H, or a linear or branched $C_{1-5}$ alkyl group; X is a halogen and in some embodiments may be Cl, Br, or I; M' is an alkali metal and in some embodiments may be selected from the group consisting of Li, Na, K, Rb, and Cs; and Z is one or more neutral ligands and in some embodiments may be at least one selected from the group consisting of DME, THF, 2-methoxyethyl ether, ammonia, pyridine, N,N,N',N'-tetramethyl-1,2-ethylenediamine, tricyclohexylphosphine, triphenylphosphine, 1,2-Bis(diphenylphosphino)ethane, 1,3-Bis(diphenylphosphino)propane. As mentioned above, in some embodiments any neutral ligand commonly known in the art may be used for Z, preferably one that does not interfere with the synthesis of $M(DAD)_2$.

In some embodiments, in Reaction Formula 1, a reaction mixture is prepared by mixing a diazadiene ligand compound and a halogenated metal compound represented by $MX_2$ or halogenated metal complex compound represented by $ZMX_2$ in an organic solvent. The halogenated metal compound or halogenated metal complex compound may be dissolved in the organic solvent or may be dispersed in the form of powder in the organic solvent. Then, an alkali metal may be added with stirring. The added alkali metal may be dissolved while causing an exothermic reaction. After the added alkali metal is completely dissolved, a salt insoluble in the organic solvent is removed by filtering. After removing the organic solvent, a liquid precursor composition is obtained by purification such as by a single or multiple step(s) of reduced-pressure distillation.

In some embodiments, a different order of the addition of the reactants is utilized as in Reaction Formula 2. The halogenated metal compound represented by $MX_2$ or halogenated metal complex compound represented by $ZMX_2$ can be mixed with an alkali metal in an organic solvent. Herein, the halogenated metal compound represented by $MX_2$ or halogenated metal complex compound represented by $ZMX_2$ may be dissolved in the organic solvent or may be dispersed in the form of powder in the organic solvent. During this step, the alkali metal is not dissolved but remains in a solid state. Then, a diazadiene ligand DAD may be slowly added to the mixture with stirring. The alkali metal may be dissolved while causing an exothermic reaction. Then, a salt insoluble in the organic solvent is removed by filtering. After removing the organic solvent, a liquid precursor composition may be obtained by purification, such as by a single or multiple step(s) of reduced-pressure distillation.

In some embodiments, the organic solvent may be a non-polar or weakly polar organic solvent, without limitation. By way of example, the organic solvent may include tetrahydrofuran (THF), 1, 2-dimethoxyethane (DME), or 2-methoxyethyl ether, but is not limited thereto.

The reaction may be performed in the presence of an inert gas such as a nitrogen gas ($N_2$) or an argon gas (Ar) in order to suppress a reaction with atmospheric moisture or, but may not be limited thereto.

Deposition Methods

In a third aspect of the present disclosure, methods are provided for forming layers using the provided liquid precursor compositions, such as vapor deposition methods. For example, the liquid precursor composition can be used in CVD or ALD processes. In some embodiments, a layer comprising nickel or cobalt is deposited by CVD or ALD. In particular, a metallic layer containing about 80 at % or more of nickel or cobalt is deposited in some embodiments.

In some embodiments, a layer containing a metal or metal compound is deposited using a liquid precursor composition comprising a metal compound represented by the following Chemical Formula 1:

$M(DAD)_2$; <Chemical Formula 1> wherein in the Chemical Formula 1,

M denotes Co or Ni, and

DAD denotes a diazadiene ligand compound represented by $R^1NC(R^3)C(R^4)NR^2$, wherein each of $R^1$ to $R^4$ includes independently H; or a linear or branched $C_{1-5}$ alkyl group.

In some embodiments, a layer may be deposited by metal organic chemical vapor deposition (MOCVD) or atomic layer deposition (ALD), but deposition methods are not limited thereto.

In some embodiments of the present disclosure, a layer containing Co or Ni may be formed using a liquid precursor composition in accordance with the first aspect of the present disclosure by CVD or ALD, but not limited thereto. For example, in some embodiments to deposit a layer containing Co or Ni on a substrate, the liquid precursor composition (or a liquid source material as discussed above) is vaporized and introduced in the deposition chamber of a CVD or ALD equipment. One or more additional appropriate reactant gases may also be introduced into the deposition chamber. The vapor of the liquid precursor composition and the reactant gases are introduced onto the surface of the substrates concurrently (in the case of CVD) or alternately (in the case of ALD).

In some embodiments, a metal-containing layer is deposited on a substrate, for example by a vapor deposition process, at a deposition temperature of from about 50° C. to about 700° C., but may not be limited thereto. In some embodiments, the deposition temperature may be from about 50° C. to about 700° C., from about 50° C. to about 600° C., from about 50° C. to about 500° C., from about 50° C. to about 400° C., from about 50° C. to about 300° C., from about 50° C. to about 200° C., from about 50° C. to about 100° C., from about 50° C. to about 80° C., from about 80° C. to about 700° C., from about 100° C. to about 700° C., from about 200° C. to about 700° C., from about 300° C. to about 700° C., from about 400° C. to about 700° C., from about 500° C. to about 700° C., from about 600° C. to about 700° C., from about 100° C. to about 600° C., from about 100° C. to about 500° C., from about 100° C. to about 400° C., from about 100° C. to about 300° C., from about 150° C. to about 700° C., from about 150° C. to about 600° C., from about 150° C. to about 500° C., from about 150° C. to about 400° C., or from about 150° C. to about 300° C., but may not be limited thereto.

In some embodiments, the liquid precursor composition may be vaporized by any of a variety of ways known in the arts such as by flowing a carrier gas through a bubbler containing the liquid precursor composition, or by direct liquid injection (DLI) into a vaporizer. The carrier gas flow may be controlled, for example, by a mass flow controller (MFC). A liquid deliver system (LDS) may be used with DLI.

In some embodiments, argon (Ar), helium (He), nitrogen ($N_2$), hydrogen ($H_2$) or a gaseous mixture thereof may be used as a carrier gas for delivering the vapor of the liquid precursor composition on the substrate, and/or as a purge gas.

In order to deposit a metal or metal compound-containing layer by CVD or ALD, various gases may be used as a reactant gas in combination with vapor of the liquid precursor composition disclosed herein. Particularly, oxygen reactants such as water vapor ($H_2O$), oxygen ($O_2$) or ozone ($O_3$) may be used to deposit a metal oxide layer. Hydrogen ($H_2$), ammonia ($NH_3$), or silanes may be used as a reactant gas in order to deposit metal or metal silicide layers. Ammonia with or without plasma may be used as a reactant gas in order to deposit a metal nitride layer. But the reactant gases may not be limited thereto. Other second reactants may be selected by the skilled artisan based on the particular circumstances and the nature of the layers to be deposited. Additional reactants may also be included in order to form more complex films. In order to deposit the metal or metal compound-containing layer, in some embodiments one or more plasma reactants may be used, such as in a plasma chemical vapor deposition or plasma atomic layer deposition process, but not limited thereto.

In some embodiments, a vapor phase reactant is prepared from a liquid precursor composition wherein about 80% or more, about 85% or more, about 90% or more, or about 95% or more of the liquid precursor composition is a metal compound of Chemical Formula 1. The composition may be determined, for example, by chromatography, such as gas chromatography. As mentioned above, in some embodiments, a vapor phase reactant may be prepared from a liquid source material which comprises a liquid precursor composition as described herein.

In some embodiments, a vapor phase reactant is prepared from a liquid precursor composition comprising a metal compound of Chemical Formula 1 and having a purity of about 80% or more, about 85% or more, about 90% or more, or 95% or more, but may not be limited thereto. That is, impurities (components other than the metal compound of Chemical Formula 1) are about 20% or less, about 15% or less, about 10% or less or even about 5% or less. The purity may be determined, for example, by chromatography, such as gas chromatography.

In some embodiments of the present disclosure, a vapor phase reactant is prepared from a liquid precursor composition wherein about 80% or more, about 85% or more, about 90% or more, or 95% or more of the liquid precursor composition is the metal compound Co($^i$PrNCHCHN$^i$Pr)$_2$. In some embodiments, the liquid precursor composition is at least about 80%, about 90%, about 95% or more pure. That is, impurities (components other than the metal compound Co($^i$PrNCHCHN$^i$Pr)$_2$) are about 20% or less, about 15% or less, about 10% or less or even about 5% or less. In some embodiments, a vapor phase reactant is prepared from a liquid source material comprising a liquid precursor composition of Co($^i$PrNCHCHN$^i$Pr)$_2$ as described. Co($^i$PrNCHCHN$^i$Pr)$_2$ [abbreviation: Co($^i$Pr-DAD)$_2$] may have a molecular weight of about 339 g/mol, but may not be limited thereto.

In some embodiments of the present disclosure, a vapor phase reactant may be prepared from a liquid precursor composition wherein about 80% or more about 85% or more, about 90% or more, or 95% or more, of the liquid precursor composition is the metal compound Ni($^i$PrNCHCHN$^i$Pr)$_2$. In some embodiments, the liquid precursor composition is at least about 80%, about 90%, or about 95% or more pure. That is, impurities (components other than the metal compound of Ni($^i$PrNCHCHN$^i$Pr)$_2$) are about 20% or less, 15% or less, about 10% or less or even about 5% or less. In some embodiments, a vapor phase reactant is prepared from a liquid source material comprising a liquid precursor composition of Ni($^i$PrNCHCHN$^i$Pr)$_2$ as described. Ni($^i$PrNCHCHN$^i$Pr)$_2$ [abbreviation: Ni($^i$Pr-DAD)$_2$] may have a molecular weight of about 339 g/mol, but may not be limited thereto.

In some embodiments of the present disclosure, a vapor phase reactant may be prepared from a liquid precursor composition that substantially or essentially consists of the metal compound represented by Co($^i$PrNCHCHN$^i$Pr)$_2$, but may not be limited thereto.

In some embodiments of the present disclosure, a vapor phase reactant may be prepared from a liquid precursor composition that substantially or essentially consists of the metal compound represented by Ni($^i$PrNCHCHN$^i$Pr)$_2$, but may not be limited thereto.

As discussed above, In some embodiments, the liquid precursor composition may form part of a liquid source material. For example, the liquid precursor composition may be diluted to form a liquid source material that is vaporized for the deposition reactions. The content and purity of the liquid precursor compositions discussed above are given in relation to the liquid precursor composition and thus are given without consideration for any diluent, solvent, carrier or the like.

In some embodiments, a Co-containing thin film is deposited by CVD or ALD using a vapor phase reactant prepared from a liquid precursor composition containing metal compound represented by Co($^i$PrNCHCHN$^i$Pr)$_2$. In some embodiments, the film comprises greater than 80% Co.

In some embodiments, a CVD process for forming a Co-containing thin film comprises contacting a substrate with a vapor phase reactant comprising Co($^i$PrNCHCHN$^i$Pr)$_2$ at an appropriate deposition temperature. One or more additional reactants may be included in order to deposit the desired film. In some embodiments, an ALD process for forming a Co-containing thin film comprises alternately and sequentially contacting a substrate with a vapor phase reactant comprising Co($^i$PrNCHCHN$^i$Pr)$_2$ and at least one additional reactant at an appropriate deposition temperature. For example, a cobalt oxide film may be deposited by ALD by alternately and sequentially containing a substrate with vapor phase Co($^i$Pr-DAD)$_2$ prepared from a liquid precursor composition described herein and ozone or a different oxygen reactant. For example, the cobalt oxide film may be a Co$_3$O$_4$ film. In some embodiments, a cobalt nitride film may be deposited by ALD by alternately and sequentially containing a substrate with vapor phase Co($^i$Pr-DAD)$_2$ prepared from a liquid precursor composition described herein and ammonia or a different nitrogen reactant.

In some embodiments, a Ni-containing thin film is deposited by CVD or ALD using a vapor phase reactant prepared from a liquid precursor composition containing metal compound represented by Ni($^i$PrNCHCHN$^i$Pr)$_2$. In some embodiments, the film comprises greater than 80% Ni.

In some embodiments, a CVD process for forming a Ni-containing thin film comprises contacting a substrate with a vapor phase reactant comprising Ni($^i$PrNCHCHN$^i$Pr)$_2$ at an appropriate deposition temperature. One or more additional reactants may be included in order to deposit the desired film. In some embodiments, an ALD process for forming a Ni-containing thin film comprises alternately and sequentially contacting a substrate with a vapor phase reactant comprising Ni($^i$PrNCHCHN$^i$Pr)$_2$ and at least one additional reactant at an appropriate deposition temperature. For example, a nickel oxide film may be deposited by ALD by alternately and sequentially contacting a substrate with vapor phase Ni($^i$Pr-DAD)$_2$ prepared from a liquid precursor composition described herein and ozone or a different oxygen reactant. In some embodiments, a nickel nitride film may be deposited by ALD by alternately and sequentially contacting a substrate with vapor phase Ni($^i$Pr-DAD)$_2$ prepared from a liquid precursor composition described herein and ammonia or a different nitrogen reactant.

EXAMPLES

Hereinafter, the present disclosure will be explained in detail with reference to examples. However, the following examples are provided for understanding of the present disclosure but are not intended to limit the present disclosure.

As mentioned above, all commonly known methods may be used to measure elements contained in a liquid precursor composition. In some embodiments, a chromatography method may be used to separate the components and determine contents of the components. In the following Examples and Comparative Examples the contents of the components were determined by comparing the areas of the peaks of chromatograms measured by a gas chromatography (GC) using a flame ionization detector (FID).

Example 1: Preparation 1 of Liquid Precursor Composition Containing 90% or More of Co($^i$Pr-DAD)$_2$ (Via Addition of 2 Equivalents of Na First and then Addition of 2 Equivalents of $^i$Pr-DAD, Using DME Solvent)

Pieces of sodium 70.8 g (3.08 mol, 2 equivalents) were added into 1 liter (L) of 1,2-dimethoxyethane (DME) in a 10 L Schlenk flask under N$_2$ atmosphere. Anhydrous CoCl$_2$ 200 g (1.54 mol, 1 equivalent) was dispersed in 2 L of DME in another 5 L Schlenk flask to prepare a suspension. The CoCl$_2$ suspension was slowly added using a cannula into the 10 L flask containing the sodium pieces with stirring. A $^i$Pr-DAD solution was prepared by dissolving 432 g (3.08 mol, 2 equivalents) of $^i$Pr-DAD in 1 L of DME, which was slowly added into the above 10 L flask in which stirring was being performed at room temperature, to prepare a mixed solution. The mixed solution was further stirred for 24 hours at room temperature, and the DME solvent and other volatile components were removed under reduced pressure. Then, the resultant mixture was dissolved by adding 3 L of anhydrous n-hexane. The mixture dissolved in the n-hexane was filtered through Celite pad and glass frit. The n-hexane was removed from the filtrate under reduced pressure, and 333 g of a dark brown liquid was obtained. Reduced-pressure distillation at 0.3 torr was performed three (3) times to finally obtain 235 g [45.5% yield as Co($^i$Pr-DAD)$_2$] of a yellow-brown liquid as the liquid precursor composition.

Figure 4A:
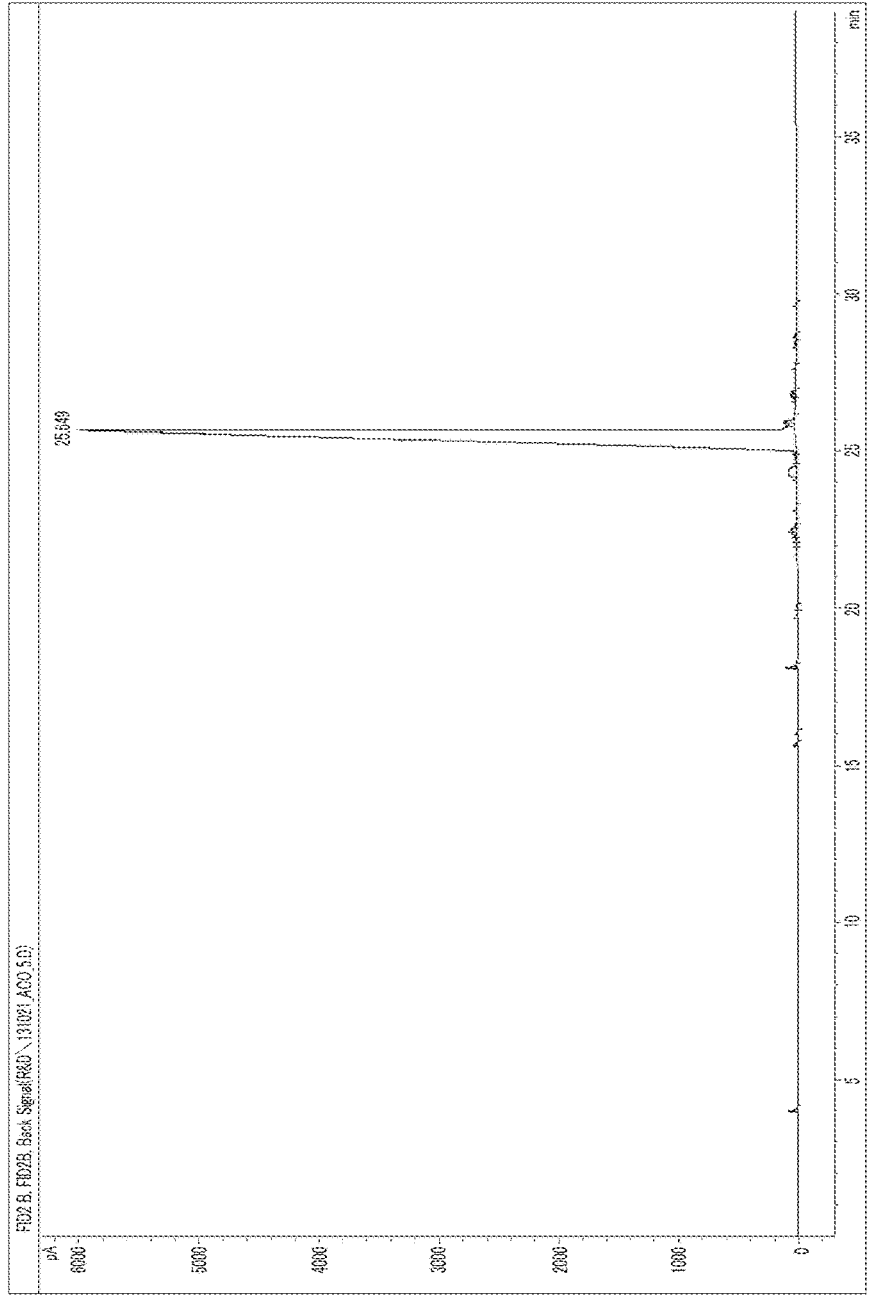
Figure 5:
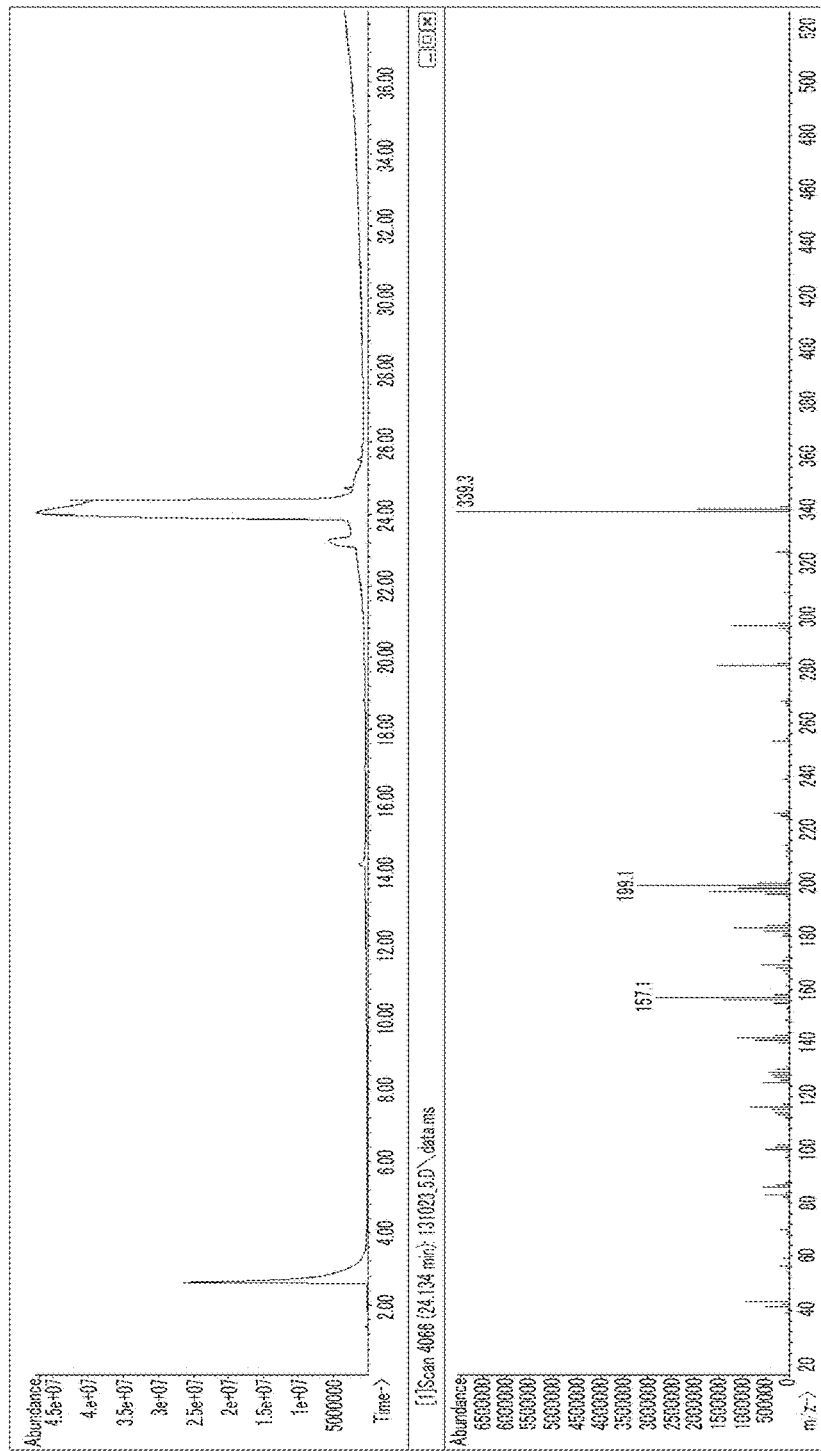
FIG. 5 shows a gas chromatography-mass spectroscopy (GC-MS) analysis result of the liquid precursor composition containing $Co(^iPr-DAD)_2$ which was prepared in accordance with Example 1.

The resulting liquid precursor composition containing Co($^i$Pr-DAD)$_2$ was analyzed using a gas chromatography-flame ionization detector (GC-FID), and a gas chromatography-mass spectroscopy (GC-MS), and the resulting chromatogram and mass spectrum obtained by analysis were as shown in FIG. 4A and FIG. 4B and FIG. 5, respectively. Agilent 7890A with HP-5 column and a FID and Agilent 7890A/5975C with HP-5MS column (GC-MS) were used as analysis instruments. A sample was injected while a temperature at a sample inlet was maintained at 200° C., and a temperature of the FID was maintained at 300° C. A temperature of a GC oven was maintained at 100° C. for 5 minutes after the sample was injected and then increased from 100° C. to 265° C. at a rate of 5° C. per minute.

FIG. 4A and FIG. 4B show the chromatogram and the area % of the peaks in the chromatogram according to the retention time obtained from a gas chromatography-flame ionization detector (GC-FID) analysis of a liquid precursor composition prepared in accordance with Example 1, and FIG. 5 shows a gas chromatography-mass spectroscopy (GC-MS) analysis result of the liquid precursor composition prepared in accordance with Example 1. It can be seen from the results shown in FIG. 4A and FIG. 4B that the content of the main component is 96.5% of the total by comparison of the areas of the chromatogram peaks. It can be seen from the result shown in FIG. 5 that the molecular mass of the main component is 339 g/mol, which corresponds to that of Co($^i$Pr-DAD)$_2$.

Gas chromatogram: The area of the peak at the retention time of 25.649 (min) was measured as 96.5% of the total peak areas.

Mass spectrum value (m/z): 32.1, 43.2, 56.2, 70.2, 86.0, 100.0, 116.1, 125.2, 133.6, 142.1, 157.1, 169.3, 183.1, 199.1, 214.1, 226.1, 239.1, 253.1, 268.1, 281.1, 296.1, 309.2, 324.3, 339.3, 353.2, 362.1, 378.3, 394.2, 405.2.

Example 2: Preparation 2 of Liquid Precursor Composition Containing 90% or More of Co($^i$Pr-DAD)$_2$ (Via Addition of 2 Equivalents of Li First and then Addition of 2 Equivalents of $^i$Pr-DAD, Using DME Solvent)

Lithium (Li) 5.3 g (0.770 mol, 2 equivalents) was added into 500 mL of DME in a 3 L Schlenk flask under N$_2$ atmosphere. Anhydrous CoCl$_2$ 50 g (0.385 mol, 1 equivalent) was dispersed in 200 mL of DME in another Schlenk flask to prepare a suspension. The CoCl$_2$ suspension was slowly added using a cannula into the 3 L flask containing lithium with stirring. An $^i$Pr-DAD solution was prepared by dissolving 108 g (0.770 mol, 2 equivalents) of $^i$Pr-DAD in 500 mL of DME, which was slowly added with stirring into the 3 L flask in which stirring was being performed at room temperature, to prepare a mixed solution. The mixed solution was further stirred for 12 hours at room temperature, and the DME solvent and other volatile components were removed under reduced pressure. Then, the resultant mixture was dissolved by adding 1.5 L of anhydrous n-hexane. The mixture dissolved in the n-hexane was filtered through Celite pad and glass frit. The n-hexane was removed from the filtrate under reduced pressure, and 110 g of a dark brown liquid was obtained. Reduced-pressure distillation at 0.3 torr was performed 3 times to finally obtain 60 g [46.2% yield as Co($^i$Pr-DAD)$_2$] of a yellow-brown liquid.

Figure 6A:
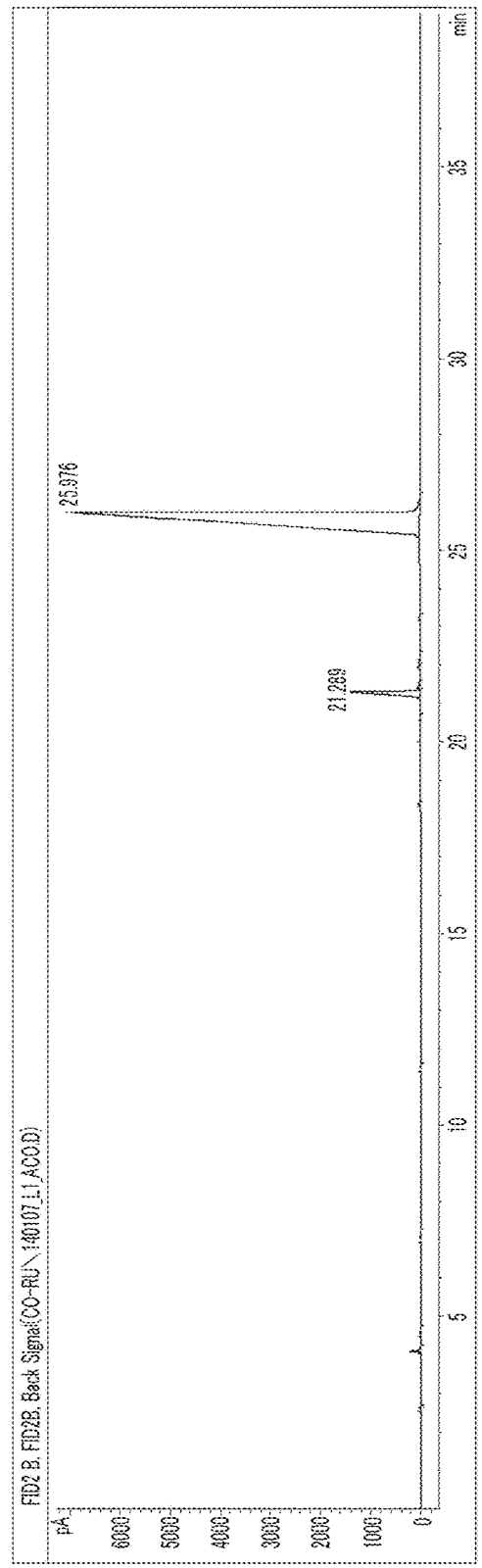

The finally obtained liquid precursor composition containing Co($^i$Pr-DAD)$_2$ was analyzed using the same GC-FID as used in Example 1, and the analysis results were as shown in FIG. 6A and FIG. 6B. It could be seen from the results shown in FIG. 6A and FIG. 6B that in the liquid precursor composition prepared in accordance with Example 2, the content of the main component is 93.9% of the total with respect to the areas of the chromatogram peaks.

Gas chromatogram: Significant peaks appeared at 21.289 (min) and 25.976 (min). The area of the peak at 25.976 (min) was measured as 93.9% of the total peak areas.

Comparative Example 1: Preparation of Liquid Precursor Composition Containing Less than 60% of Co($^i$Pr-DAD)$_2$ (Via First Reaction Between 2 Equivalents of Li and 2 Equivalents of $^i$Pr-DAD, Using THF Solvent)

$^i$Pr-DAD 432 g (3.08 mol, 2 equivalents) and lithium (Li) 21.38 g (3.08 mol, 2 equivalents) were added into 3 L of THF in a 10 L Schlenk flask under N$_2$ atmosphere for reaction to prepare an in-situ prepared solution. Anhydrous CoCl$_2$ 200 g (1.54 mol, 1 equivalent) was dispersed in 1 L of THF in another Schlenk flask to prepare a suspension. The suspension was slowly added using a cannula into the 10 L flask containing the in-situ prepared solution with stirring to prepare a mixed solution. The mixed solution was further stirred for 12 hours at room temperature, and the THF solvent and other volatile components were removed under reduced pressure. Then, the resultant mixture was dissolved by adding 3 L of anhydrous n-hexane. The mixture dissolved in the n-hexane was filtered through Celite pad and glass frit. The n-hexane was removed from the filtrate reduced pressure, and 420 g of a dark brown liquid was obtained. Reduced-pressure distillation at 0.3 torr was performed 5 times to finally obtain 37 g [7.1% yield as Co($^i$Pr-DAD)$_2$] of a yellow-brown liquid.

Figure 7A:
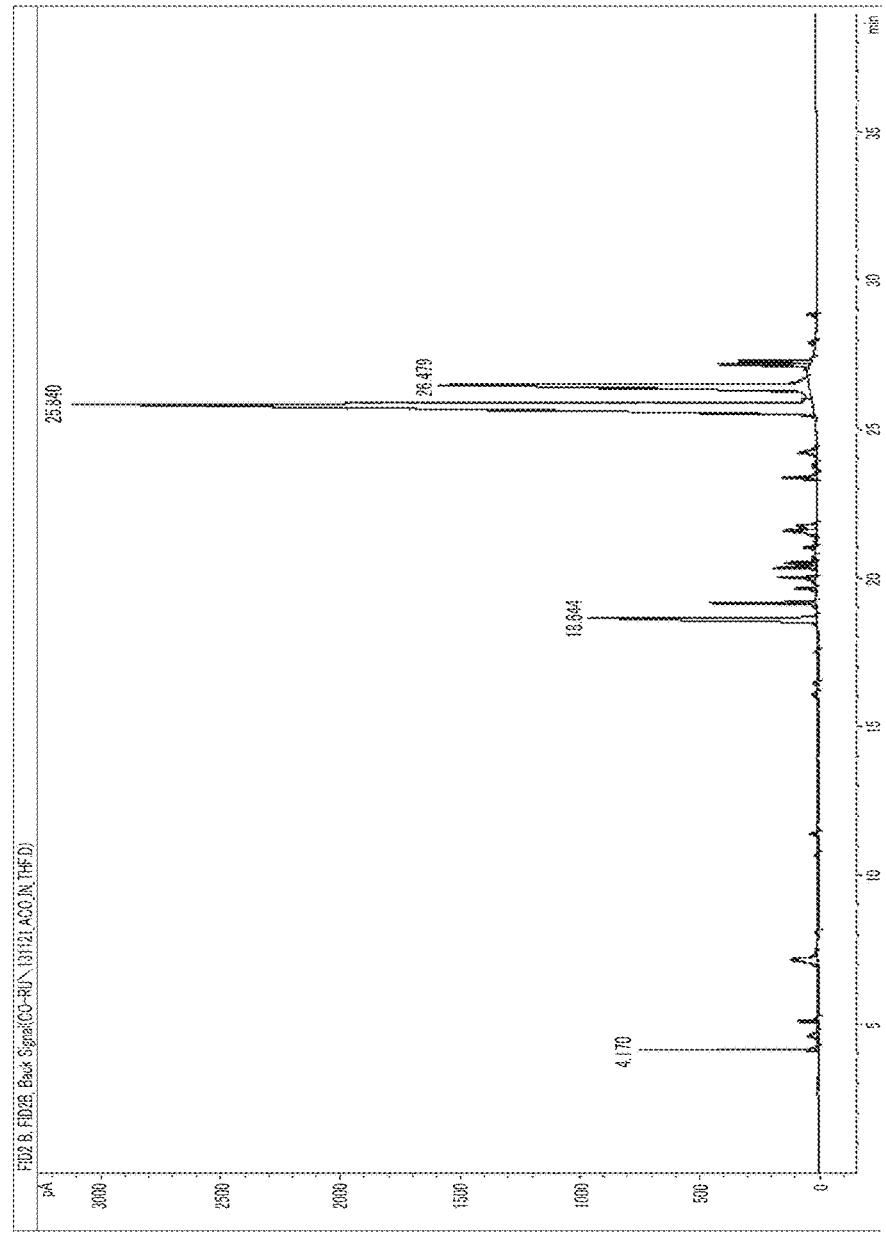
Figure 8:
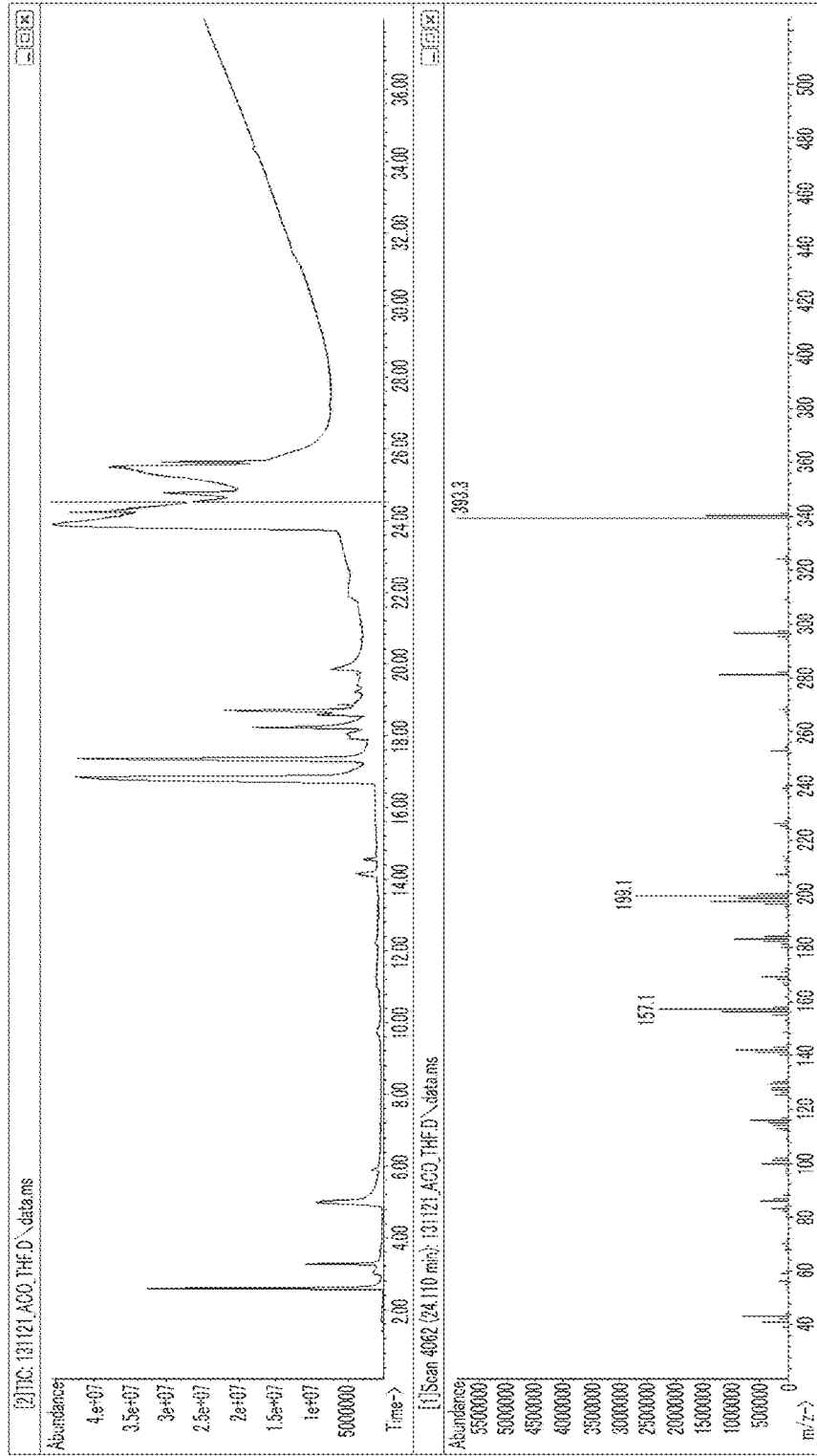
FIG. 8 shows a GC-MS analysis result of the liquid precursor composition containing $Co(^iPr-DAD)_2$ which was prepared in accordance with Comparative Example 1.

The finally obtained liquid precursor composition containing Co($^i$Pr-DAD)$_2$ was analyzed using the same GC-FID and GC-MS as used in Example 1, and the analysis results were as shown in FIG. 7A and FIG. 7B and FIG. 8, respectively. It could be seen from the GC-MS result shown in FIG. 8 that the molecular mass of the main component is 339 g/mol, which corresponds to that of Co($^i$Pr-DAD)$_2$. However, it could be seen from the GC-FID results shown in FIG. 7A and FIG. 7B that the liquid precursor composition obtained in accordance with Comparative Example 1 contains the metal compound, as the main element, in a content of 52.4% of the total and contains a lot of impurities despite reduced-pressure distillation repeated 5 times.

Gas chromatogram: Peaks appeared at 4.170 (min), 18.644 (min), 19.154 (min), 25.840 (min), 26.479 (min), and 27.163 (min). The area of the peak at 25.840 (min) was measured as 52.4% of the total peak areas.

Mass spectrum value (m/z): 43.1, 56.1, 70.1, 86.0, 100.0, 116.0, 129.1, 142.0, 157.1, 169.2, 183.1, 199.1, 214.1, 226.1, 239.1, 253.1, 268.1, 281.1, 296.1, 309.2, 324.3, 339.3, 355.2, 378.0, 394.2, 405.1, 415.0, 429.1, 479.2, 508.9.

It is difficult to obtain a NMR signal from Co($^i$Pr-DAD)$_2$. Therefore, a purity could not be determined by a typical NMR analysis method. In Examples herein, the composition substantially or essentially consisting of an component at a mass/charge ratio (m/z) of 339 was obtained.

Example 3: Preparation 1 of Liquid Precursor Composition Containing 90% or More of Ni($^i$Pr-DAD)$_2$ (Via Addition of 2 Equivalents of $^i$Pr-DAD First and then Addition of 2 Equivalents of Li, Using THF Solvent)

Anhydrous NiBr$_2$ 220 g (1.007 mol, 1 equivalent) and $^i$Pr-DAD 282 g (2.014 mol, 2 equivalents) were added into 3 L of THF in a 5 L Schlenk flask under N$_2$ atmosphere, and a resultant mixed solution was stirred at room temperature for 3 hours. Then, lithium (Li) 14.0 g (2.014 mol, 2 equivalents) was slowly added with stirring to prepare a mixed solution. The mixed solution was stirred at room temperature for 12 hours, and the THF solvent and other volatile components were removed under reduced pressure. Then, the resultant mixture was dissolved by adding 2 L of anhydrous n-hexane. The mixture dissolved in the n-hexane was filtered through Celite pad and glass frit. The n-hexane was removed from the filtrate under reduced pressure, and 268 g of a dark brown liquid was obtained. Reduced-pressure distillation at 0.3 torr was performed 3 times to finally obtain 240 g [70.7% yield as Ni ($^i$Pr-DAD)$_2$] of a yellow-brown liquid.

Figure 9A:
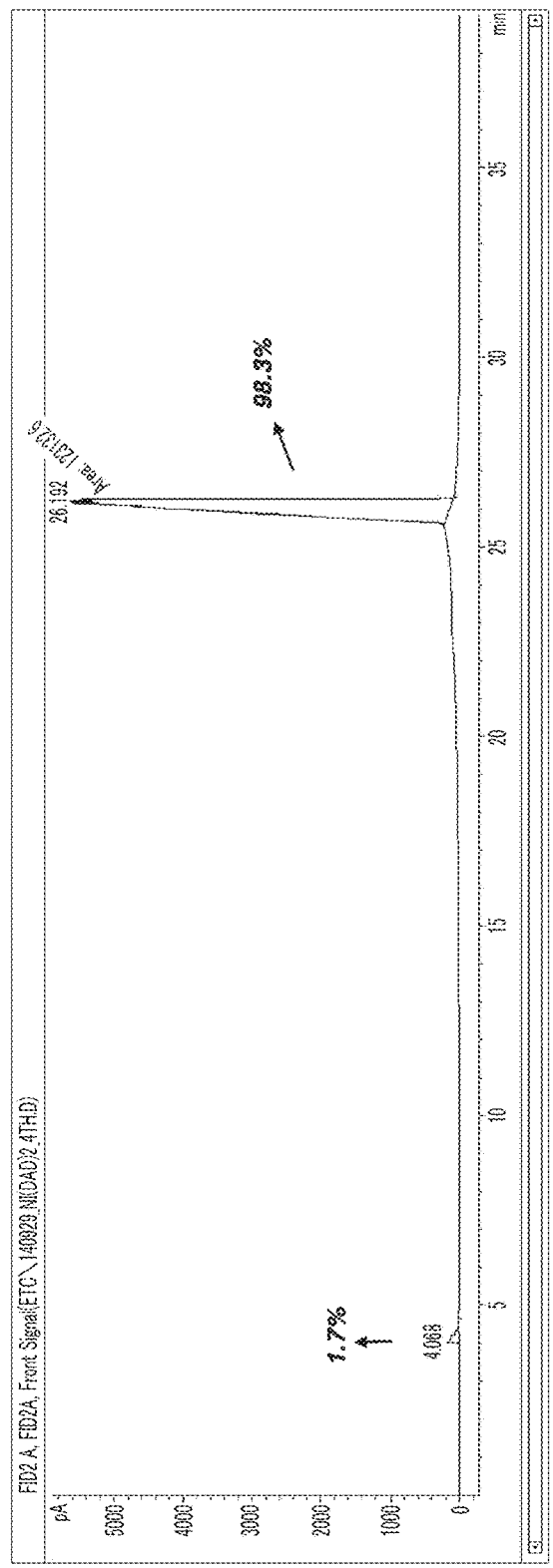
Figure 10:
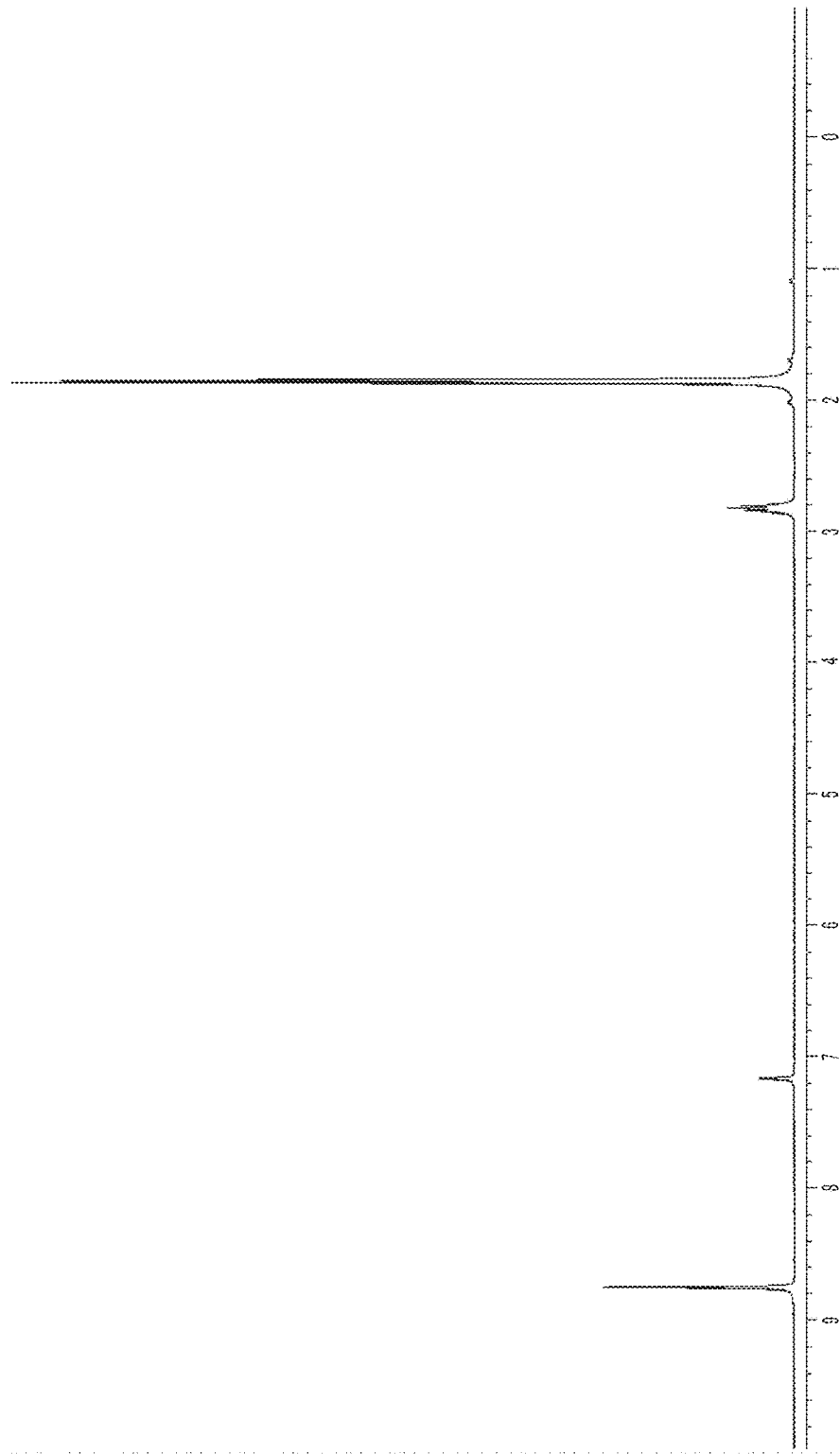
FIG. 10 shows a NMR spectrum of the liquid precursor composition containing $Ni(^iPr-DAD)_2$ which was prepared in accordance with Example 3.

The finally obtained liquid precursor composition containing Ni($^i$Pr-DAD)$_2$ was analyzed using the same GC-FID as used in Example 1, and the analysis result was as shown in FIG. 9A and FIG. 9B. It could be seen from the result shown in FIG. 9A and FIG. 9B that the liquid precursor composition contains a single compound represented by Ni($^i$Pr-DAD)$_2$ as a main component in a content of 98.3% of the total. A nuclear magnetic resonance (NMR) spectrum of the liquid precursor composition is shown in FIG. 10. NMR signals other than those of Ni($^i$Pr-DAD)$_2$ are hardly observed.

Gas chromatogram: Significant peaks appeared at 4.068 (min) and 26.192 (min). The area of the peak at 26.192 (min) was measured as 98.3% of the total peak areas.

$^1$H-NMR (400 MHz, C$_6$D$_6$, 25° C.) δ 8.747 (s, 4H, NCH), 2.823 (septet, 4H, CH(CH$_3$)$_2$), 1.853 (d, 24H, CH(CH$_3$)$_2$).

Example 4: Preparation 2 of Liquid Precursor Composition Containing 90% or More of Ni($^i$Pr-DAD)$_2$ (Via Addition of 2 Equivalents of Na First and then Addition of 2 Equivalents of $^i$Pr-DAD, Using THF Solvent)

Sodium (Na) 21.1 g (0.915 mol, 2 equivalents) was added into 1 L of THF in a 3 L Schlenk flask under N$_2$ atmosphere. Anhydrous NiBr$_2$ 100 g (0.458 mol, 1 equivalent) was dispersed in 500 mL of THF in another Schlenk flask to prepare a suspension. The suspension was slowly added using a cannula into the 3 L flask containing sodium with stirring. A $^i$Pr-DAD solution was prepared by dissolving 128.3 g (0.915 mol, 2 equivalents) of $^i$Pr-DAD in 500 mL of THF, which was slowly added with stirring into the 3 L flask in which stirring was being performed at room temperature, to prepare a mixed solution. The mixed solution was stirred at room temperature for 12 hours, and the THF solvent and other volatile components were removed under reduced pressure. Then, the resultant mixture was dissolved by adding 1 L of anhydrous n-hexane. The mixture dissolved in the n-hexane was filtered through Celite pad and glass frit. The n-hexane was removed from the filtrate under reduced pressure, and 110 g of a dark brown liquid was obtained. Reduced-pressure distillation at 0.3 torr was performed 3 times to finally obtain 45 g [28.9% yield as Ni ($^i$Pr-DAD)$_2$] of a dark brown liquid.

Figure 11A:
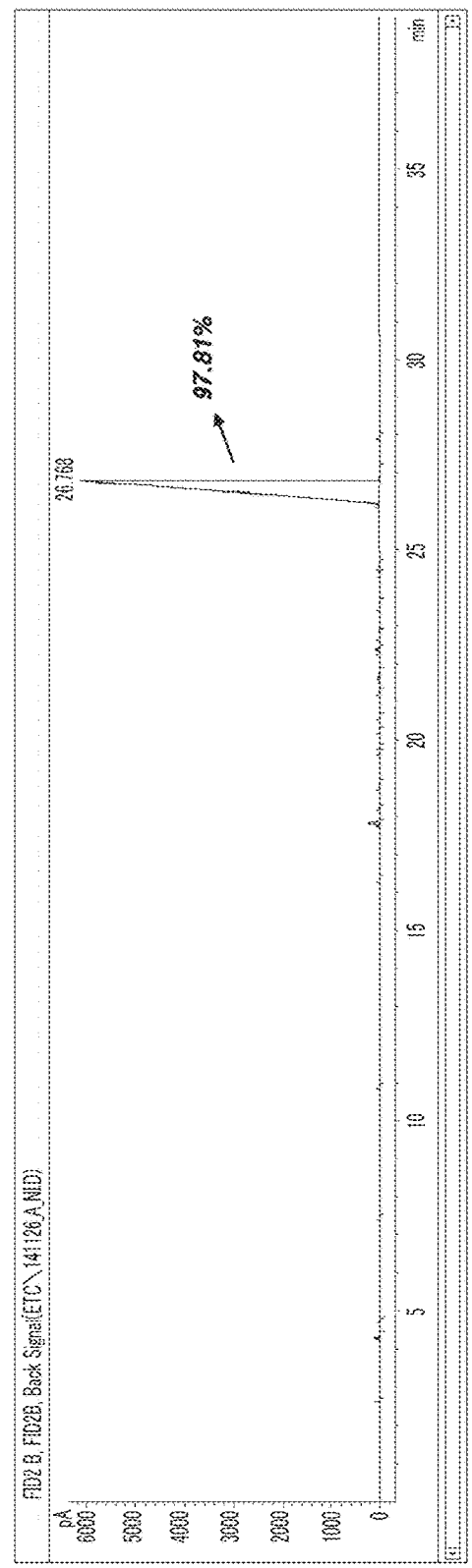
Figure 12:
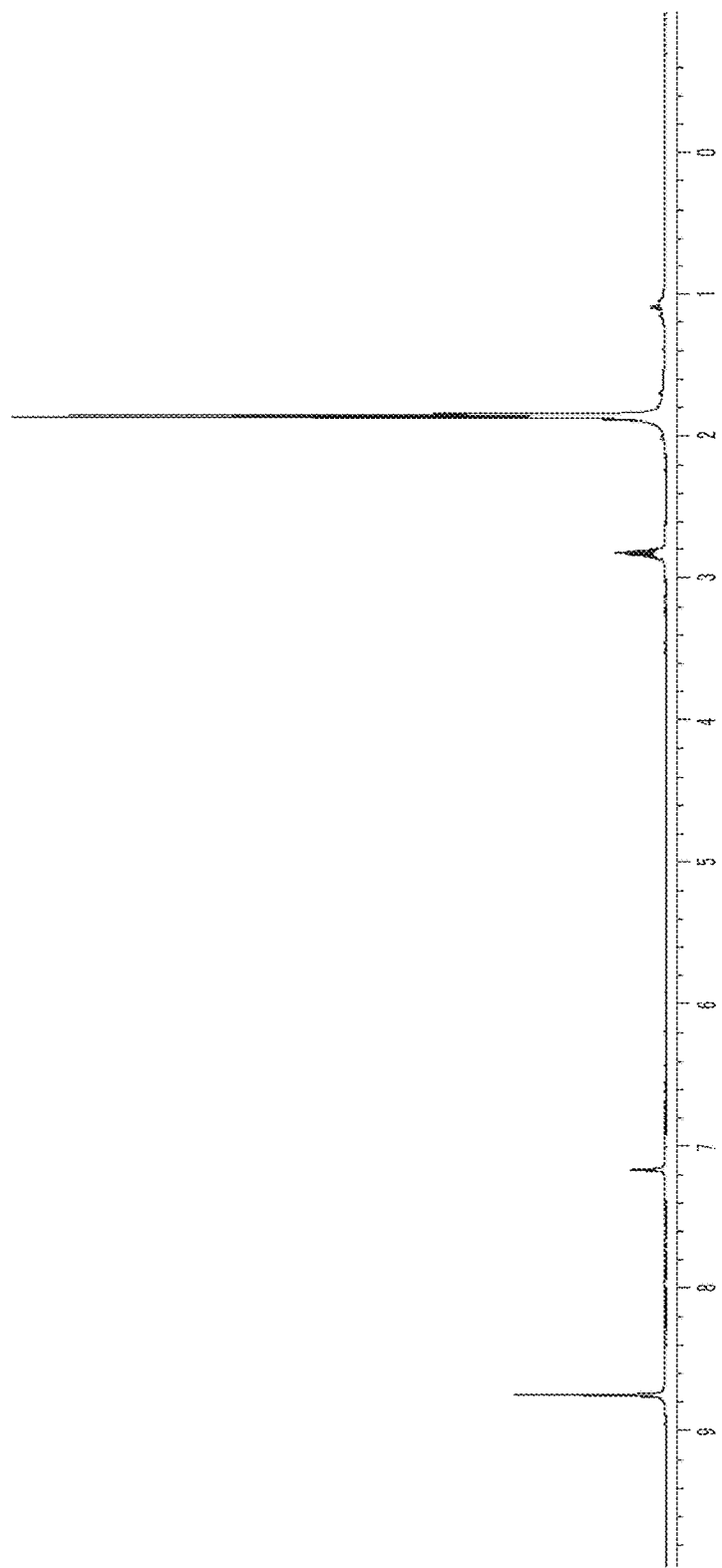
FIG. 12 shows a NMR spectrum of the liquid precursor composition containing $Ni(^iPr-DAD)_2$ which was prepared in accordance with Example 4.

The finally obtained liquid precursor composition containing Ni($^i$Pr-DAD)$_2$ was analyzed using the same GC-FID as used in Example 1, and the analysis result is shown in FIG. 11A and FIG. 11B. It can be seen from the result shown in FIG. 11A and FIG. 11B that the liquid precursor composition contains a main component in a content of 97.8% of the total. An NMR spectrum of the liquid precursor composition is shown in FIG. 12. NMR signals other than those of Ni($^i$Pr-DAD)$_2$ are hardly observed.

Gas chromatogram: Significant peaks appeared at 4.328 (min), 17.819 (min), and 26.768 (min). The area of the peak at 26.768 (min) was measured as 97.8% of the total peak areas.

$^1$H-NMR (400 MHz, C$_6$D$_6$, 25° C.) δ 8.744 (s, 4H, NCH), 2.825 (septet, 4H, CH(CH$_3$)$_2$), 1.853 (d, 24H, CH(CH$_3$)$_2$).

Example 5: Preparation 3 of Liquid Precursor Composition Containing 90% or More of Ni($^i$Pr-DAD)$_2$ (Via Addition of 2 Equivalents of Li First and then Addition of 2 Equivalents of $^i$Pr-DAD, Using THF Solvent Lithium (Li) 6.4 g (0.92 mol, 2 equivalents) was added into 1 L of THF in a 3 L Schlenk flask under N$_2$ atmosphere. Anhydrous NiBr$_2$ 100 g (0.458 mol, 1 equivalent) was dispersed in 500 mL of THF in another Schlenk flask to prepare a suspension. The suspension was slowly added using a cannula into the 3 L flask containing lithium with stirring. An $^i$Pr-DAD solution was prepared by dissolving 128.3 g (0.915 mol, 2 equivalents) of $^i$Pr-DAD in 500 mL of THF, which was slowly added with stirring into the 3 L flask in which stirring was being performed at room temperature, to prepare a mixed solution. The mixed solution was stirred at room temperature for 12 hours, and the THF solvent and other volatile components were removed under reduced pressure. Then, the resultant mixture was dissolved by adding 1 L of anhydrous n-hexane. The mixture dissolved in the n-hexane was filtered through Celite pad and glass frit. The n-hexane was removed from the filtrate under reduced pressure, and 102 g of a dark brown liquid was obtained. Reduced-pressure distillation at 0.3 torr was performed 3 times to finally obtain 85 g [55.1% yield as Ni ($^i$Pr-DAD)$_2$] of a dark brown liquid.

Figure 13A:
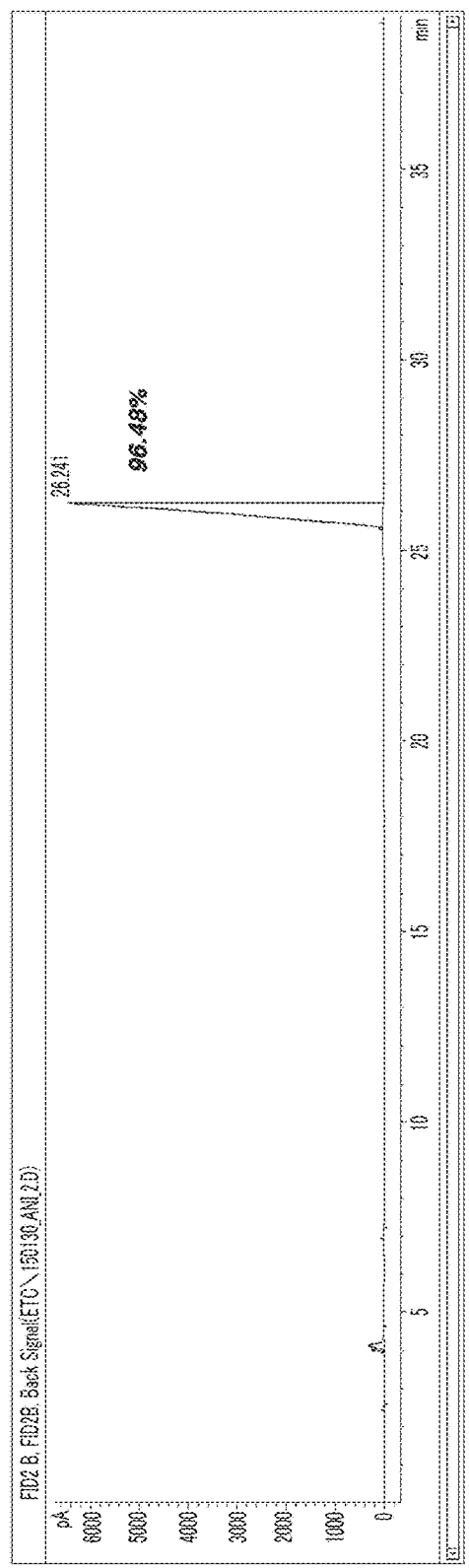
Figure 14:
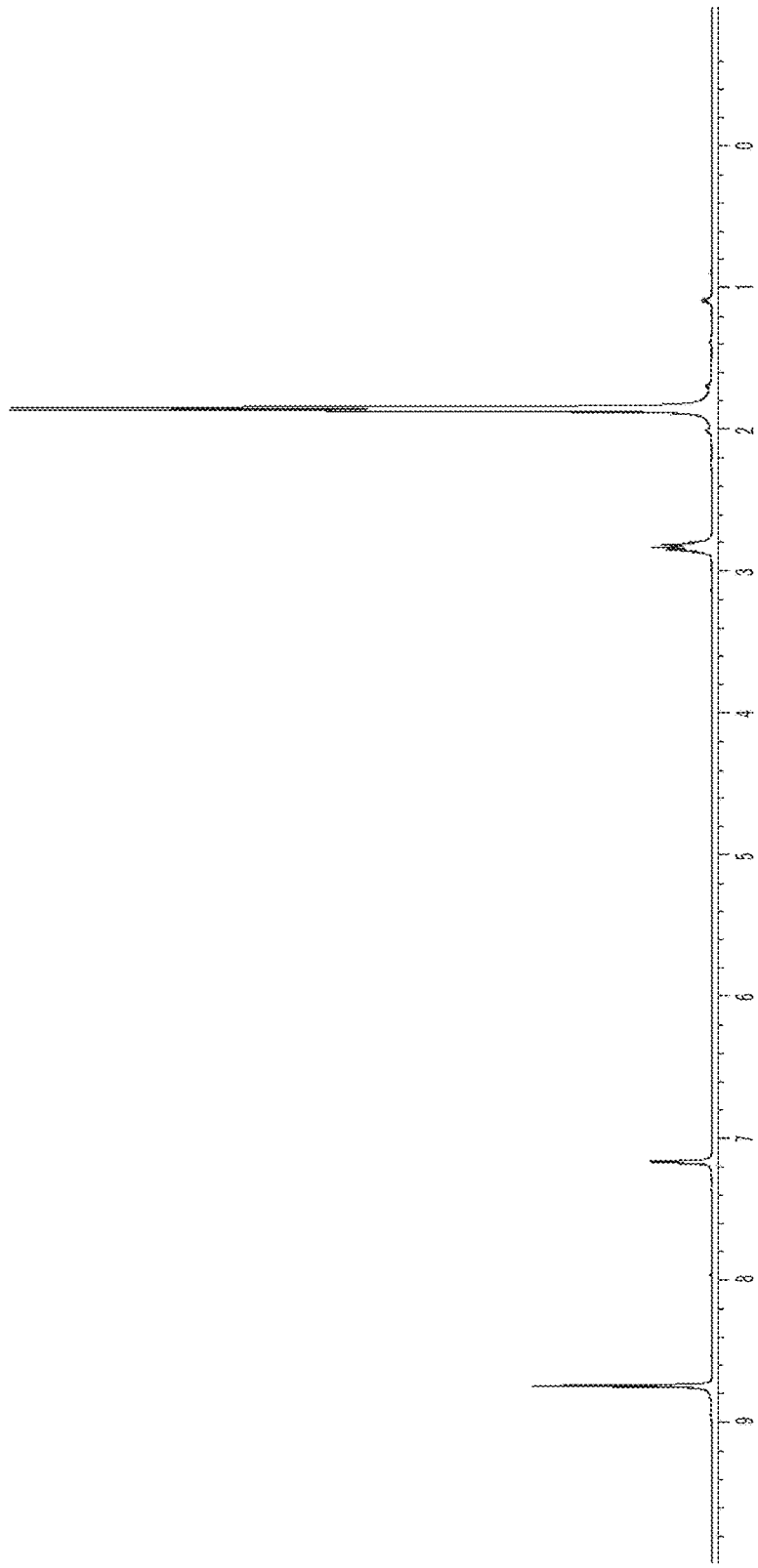
FIG. 14 shows a NMR spectrum of the liquid precursor composition containing $Ni(^iPr-DAD)_2$ which was prepared in accordance with Example 5.

The finally obtained liquid precursor composition containing Ni($^i$Pr-DAD)$_2$ was analyzed using the same GC-FID as used in Example 1, and the analysis result was as shown in FIG. 13A and FIG. 13B. It could be seen from the result shown in FIG. 13A and FIG. 13B that the liquid precursor composition contains a main component in a content of 96.5% of the total. An NMR spectrum of the liquid precursor composition is shown in FIG. 14. NMR signals other than those of Ni($^i$Pr-DAD)$_2$ are hardly observed.

Gas chromatogram: Significant peaks appeared at 4.005 (min), 4,133 (min), 7.018 (min), and 26.241 (min). The area of the peak at 26.241 (min) was measured as 96.5% of the total peak areas.

$^1$H-NMR (400 MHz, C$_6$D$_6$, 25° C.) δ 8.740 (s, 4H, NCH), 2.829 (septet, 4H, CH(CH$_3$)$_2$), 1.855 (d, 24H, CH(CH$_3$)$_2$).

Example 6: Preparation 4 of Liquid Precursor Composition Containing 90% or More of Ni($^i$Pr-DAD)$_2$ (Via Addition of 2 Equivalents of Li First and then Addition of 2 Equivalents Weight of $^i$Pr-DAD, Using DME Solvent)

Lithium (Li) 6.4 g (0.92 mol, 2 equivalents) was added into 1 L of DME in a 2 L Schlenk flask under N$_2$ atmosphere. Anhydrous NiBr$_2$ 100 g (0.458 mol, 1 equivalent) was dispersed in 500 mL of DME in another Schlenk flask to prepare a suspension. The suspension was slowly added using a cannula into the 2 L flask containing lithium with stirring. A $^i$Pr-DAD solution was prepared by dissolving 128.3 g (0.915 mol, 2 equivalents) of $^i$Pr-DAD in 500 mL of DME, which was slowly added with stirring into the 2 L flask in which stifling was being performed at room temperature, to prepare a mixed solution. The mixed solution was stirred at room temperature for 12 hours, and the DME solvent and other volatile components were removed under reduced pressure. Then, the resultant mixture was dissolved by adding 1 L of anhydrous n-hexane. The mixture dissolved in the n-hexane was filtered through Celite pad and glass frit. The n-hexane was removed from the filtrate under reduced pressure, and 150 g of a dark brown liquid was obtained. Reduced-pressure distillation at 0.3 torr was performed 2 times to finally obtain 106 g [68.3% yield as Ni ($^i$Pr-DAD)$_2$] of a dark brown liquid.

Figure 15A:
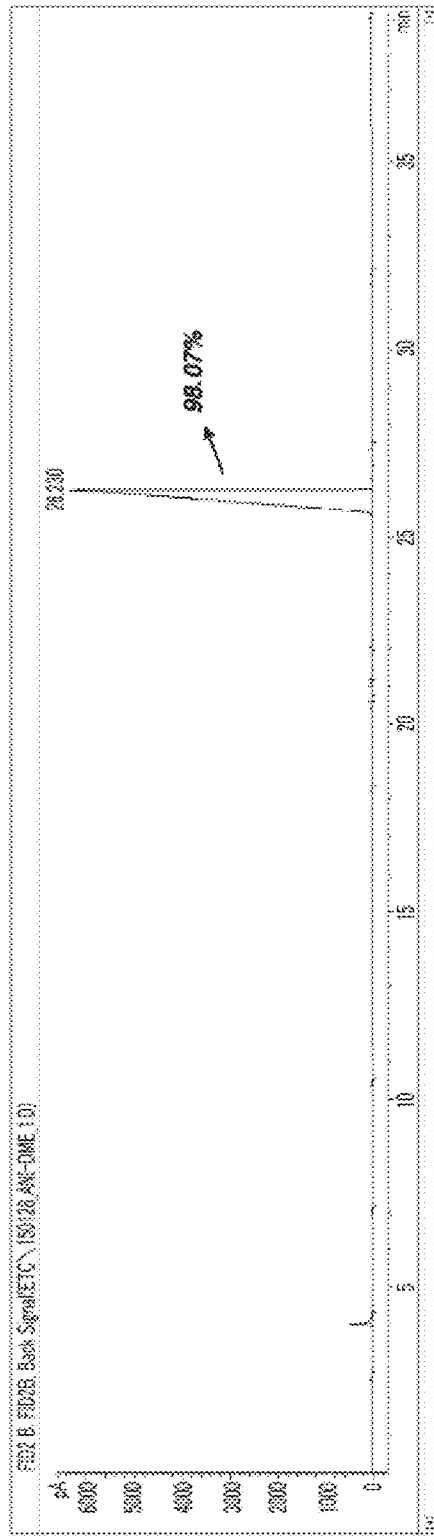
Figure 16:
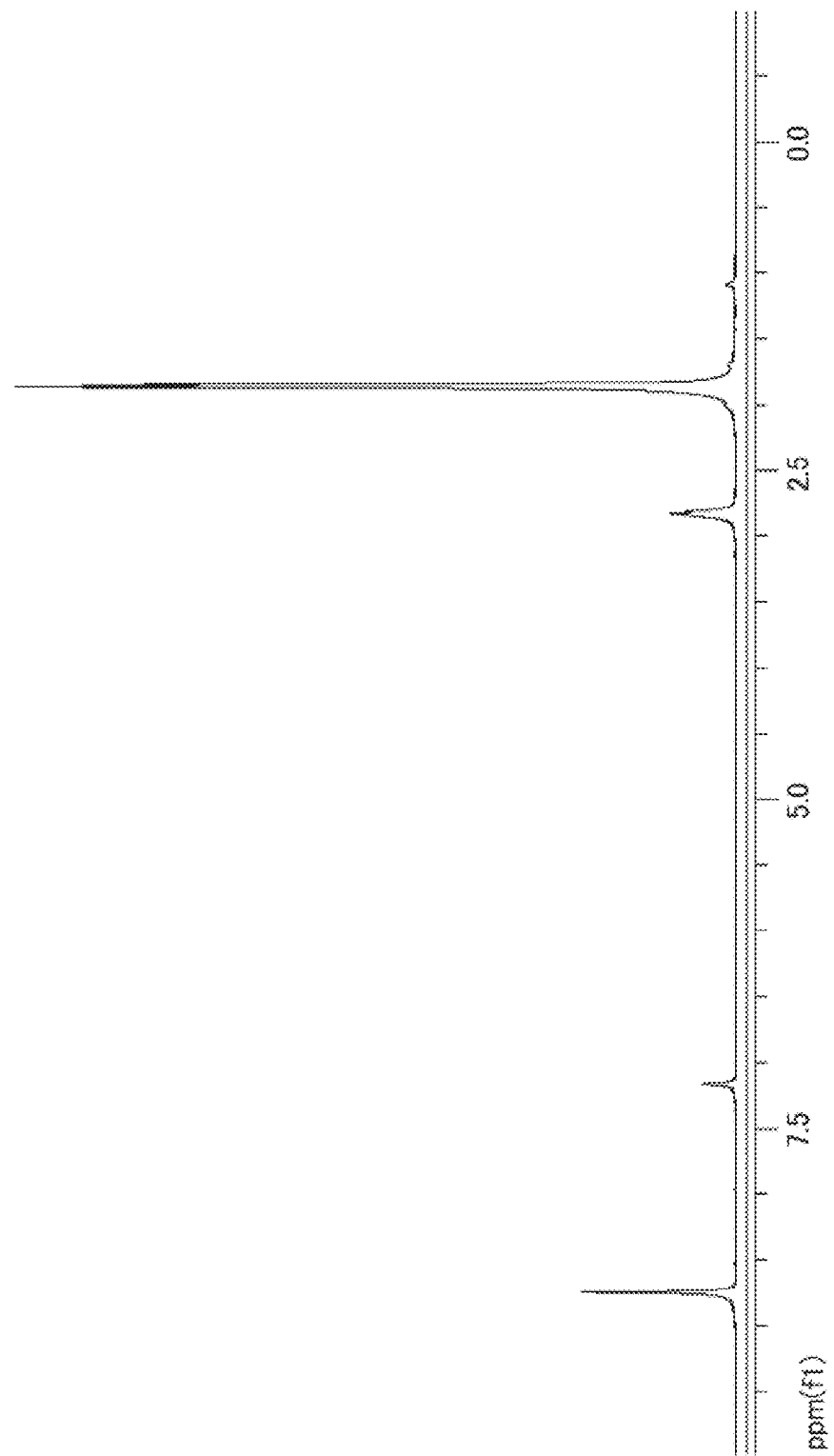
FIG. 16 shows a NMR spectrum of the liquid precursor composition containing $Ni(^iPr-DAD)_2$ which was prepared in accordance with Example 6.

The finally obtained liquid precursor composition containing Ni($^i$Pr-DAD)$_2$ was analyzed using the same GC-FID as used in Example 1, and the analysis result is shown in FIG. 15A and FIG. 15B. It could be seen from the result shown in FIG. 15A and FIG. 15B that the liquid precursor composition contains a main component in a content of 98.1% of the total. An NMR spectrum of the liquid precursor composition is shown in FIG. 16. NMR signals other than those of Ni($^i$Pr-DAD)$_2$ are hardly observed.

Gas chromatogram: Significant peaks appeared at 3.995 (min), 21.084 (min), and 26.230 (min). The area of the peak at 26.230 (min) was measured as 98.1% of the total peak areas.

$^1$H-NMR (400 MHz, C$_6$D$_6$, 25° C.) δ 8.740 (s, 4H, NCH), 2.828 (septet, 4H, CH(CH$_3$)$_2$), 1.855 (d, 24H, CH(CH$_3$)$_2$).

Comparative Example 2: Preparation of Liquid Precursor Composition Containing Less than 60% of Ni($^i$Pr-DAD)$_2$ (Via First Reaction Between 2 Equivalents of Na and 2 Equivalents of $^i$Pr-DAD, Using NiBr$_2$)

$^i$Pr-DAD 40 g (0.28 mol, 2 equivalents) and sodium (Na) 6.6 g (0.28 mol, 2 equivalents) were added into 0.3 L of THF in a 1 L Schlenk flask under N$_2$ atmosphere for reaction to prepare an in-situ prepared solution. NiBr$_2$ 31 g (0.14 mol, 1 equivalent) was dispersed in 0.2 L of THF in another 1 L Schlenk flask to prepare a suspension. The suspension was slowly added using a cannula into the 1 L flask containing the in-situ prepared solution with stirring to prepare a mixed solution. The mixed solution was further stirred for 12 hours at room temperature, and the THF solvent and other volatile components were removed under reduced pressure. Then, the resultant mixture was dissolved by adding 0.2 L of anhydrous n-hexane. The mixture dissolved in the n-hexane was filtered through Celite pad and glass frit. The n-hexane was removed from the filtrate under reduced pressure, and 44 g of a dark brown liquid was obtained. Reduced-pressure distillation at 0.5 torr was performed once and 5.5 g of a dark brown liquid was obtained. Because GC-FID and NMR spectrum indicate only a minute content of Ni($^i$Pr-DAD)$_2$ in the liquid precursor composition, further purification was not performed.

Figure 17A:
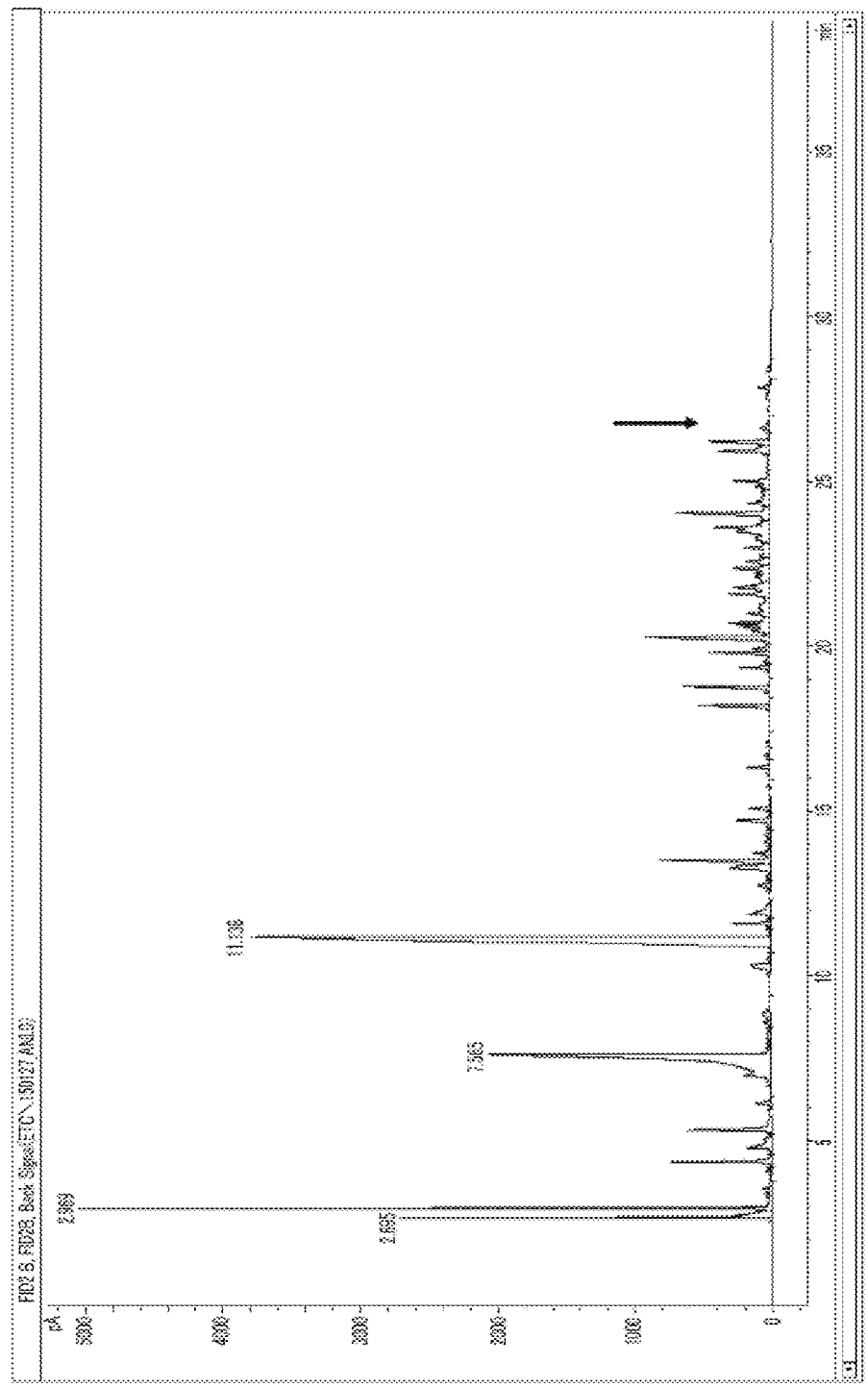
Figure 18:
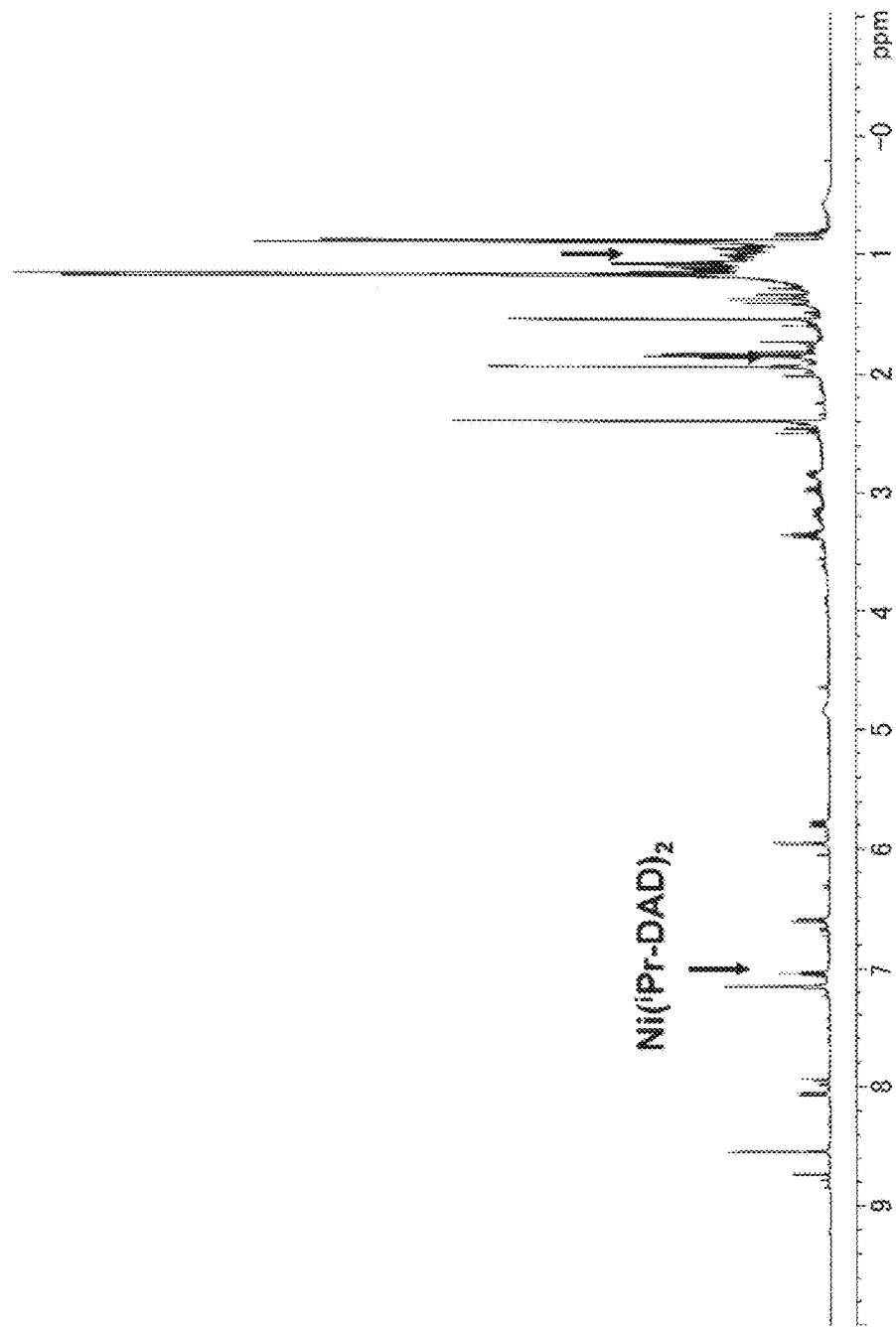
FIG. 18 shows a NMR spectrum of the liquid precursor composition containing $Ni(^iPr-DAD)_2$ which was prepared in accordance with Comparative Example 2.

The obtained liquid precursor composition was analyzed using the same GC-FID as used in Example 1, and the analysis result is shown in FIG. 17A and FIG. 17B. An NMR spectrum of the liquid precursor compositions is shown in FIG. 18. An NMR signal of Ni($^i$Pr-DAD)$_2$ is indicated by the arrow. It could be seen that the content of Ni($^i$Pr-DAD)$_2$ in this liquid composition is insignificant since the area of the peak for the signal of Ni($^i$Pr-DAD)$_2$ in the NMR spectrum is much smaller than the other peak areas. Further, it could be seen that the content of Ni($^i$Pr-DAD)$_2$ is less than 2% since an area of any peak around 26 (min) where the signal of Ni($^i$Pr-DAD)$_2$ appears in the gas chromatogram is less than 2% of the total peak areas.

Comparative Example 3: Preparation of Liquid Precursor Composition Containing Less than 60% of Ni($^i$Pr-DAD)$_2$ (Via First Reaction Between 2 Equivalents of Na and 2 Equivalents of $^i$Pr-DAD, Using (DME)NiBr$_2$)

$^i$Pr-DAD 36 g (0.26 mol, 2 equivalents) and sodium (Na) 6.0 g (0.26 mol, 2 equivalents) were added into 0.3 L of THF in a 1 L Schlenk flask under N$_2$ atmosphere for reaction to prepare an in-situ prepared solution. (DME)NiBr$_2$ 40 g (0.129 mol, 1 equivalent) was dispersed in 0.2 L of THF in another 1 L Schlenk flask to prepare a suspension. The suspension was slowly added using a cannula into the 1 L flask containing the in-situ prepared solution with stirring to prepare a mixed solution. The mixed solution was further stirred for 12 hours at room temperature, and the THF solvent and other volatile components were removed under reduced pressure. Then, the resultant mixture was dissolved by adding 0.2 L of anhydrous n-hexane. The mixture dissolved in the n-hexane was filtered through Celite pad and glass frit. The n-hexane was removed from the filtrate under reduced pressure, and 40.5 g of a dark brown liquid was obtained. Reduced-pressure distillation at 0.5 torr was performed once and 9 g of a dark brown liquid was obtained.

Figure 19A:
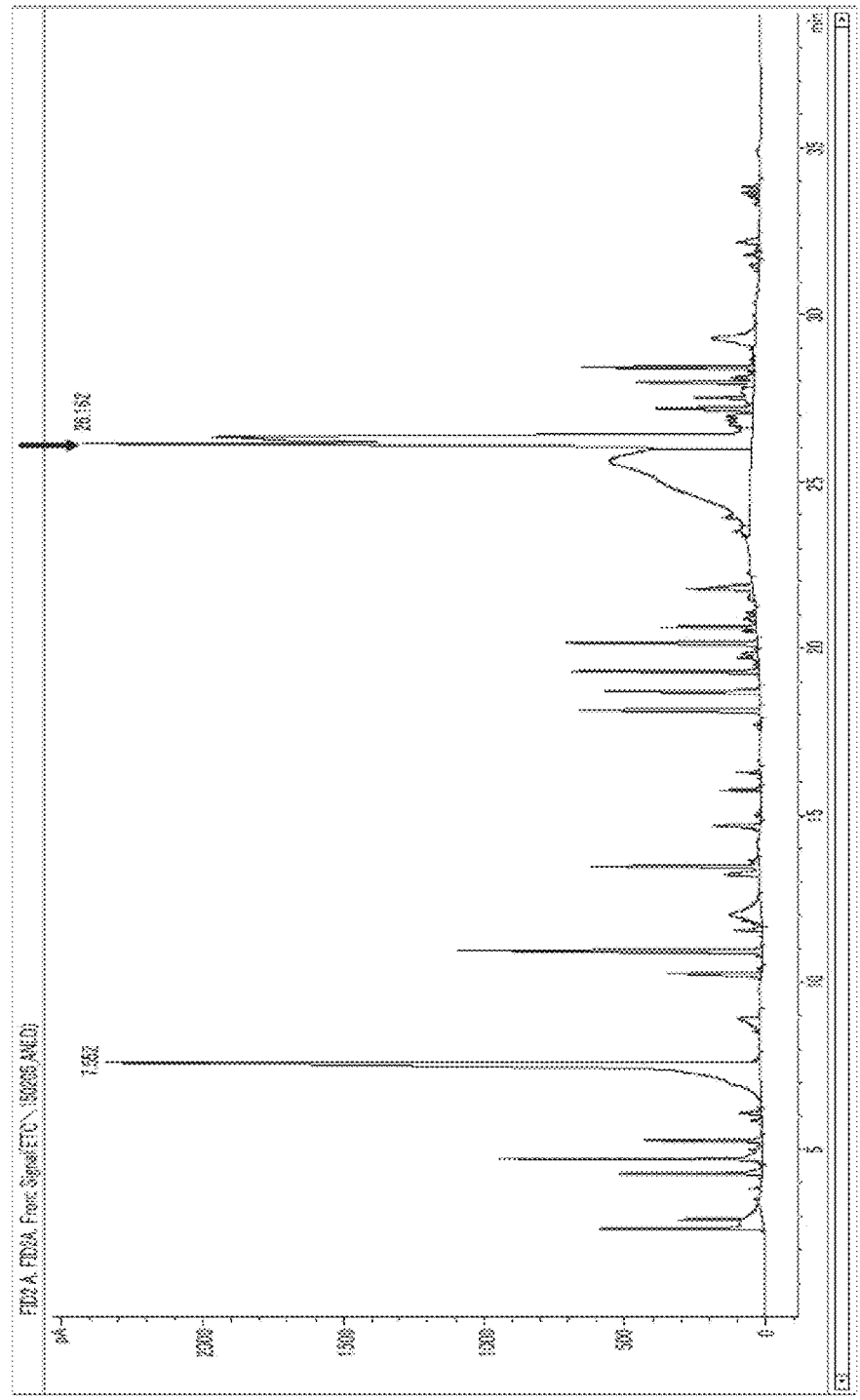
Figure 20:
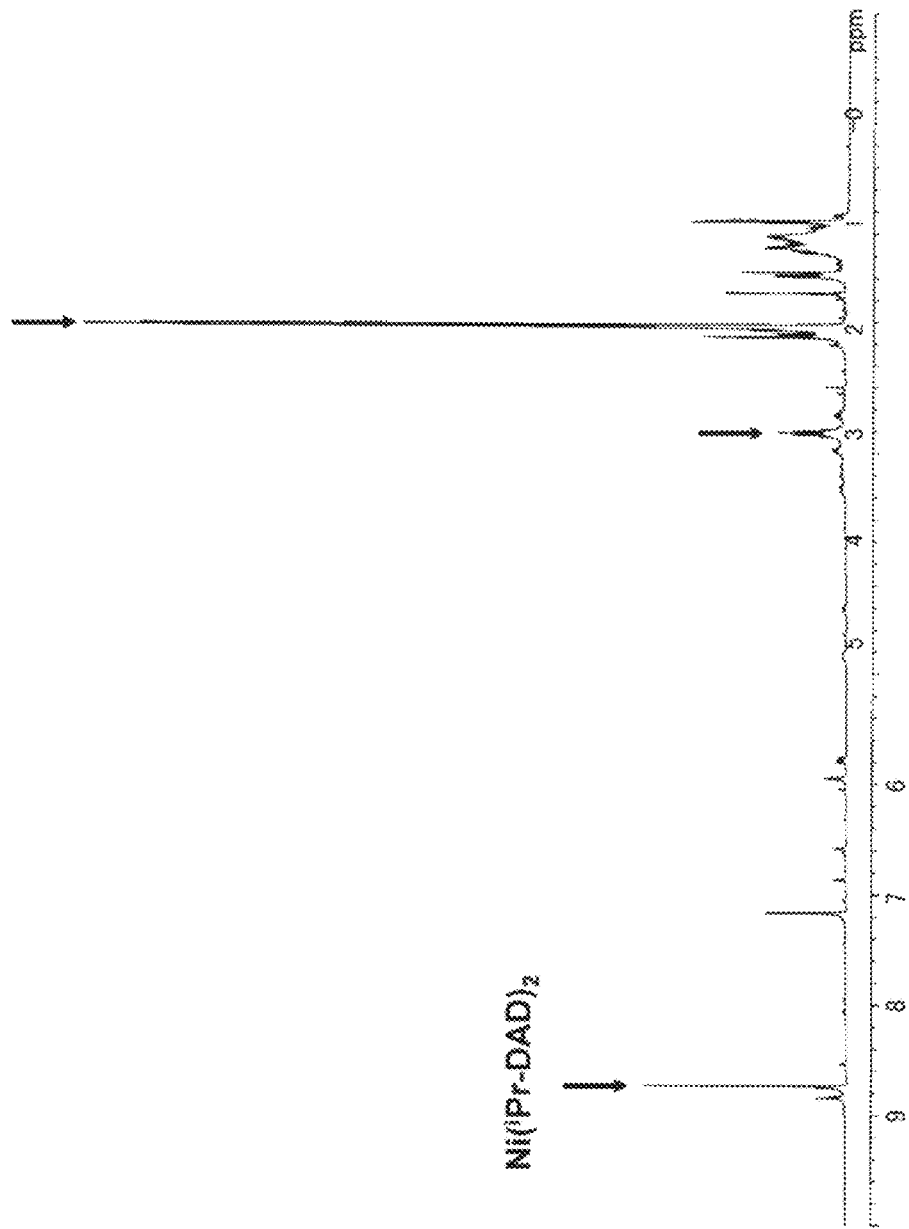
FIG. 20 shows a NMR spectrum of the liquid precursor composition containing $Ni(^iPr-DAD)_2$ which was prepared in accordance with Comparative Example 3.

The obtained liquid precursor composition was analyzed using the same GC-FID as used in Example 1, and the analysis result was as shown in FIG. 19A and FIG. 19B. An NMR spectrum of the liquid precursor composition is shown in FIG. 20, and a NMR signal of Ni($^i$Pr-DAD)$_2$ was as indicated by the arrow. It can be seen that the content of Ni($^i$Pr-DAD)$_2$ in this composition is less than 30% because the areas of the most significant peaks at 25.634 (min) and 26.162 (min) in the gas chromatogram are measured as 23.9% and 24.4%, respectively, of the total peak areas, even though it is not known which of the two peaks at 25.634 (min) and 26.162 (min) is for Ni($^i$Pr-DAD)$_2$. Further, such materials, of which peaks are so close to each other in retention time in the gas chromatogram, cannot be substantially separated by fractional distillation.

A liquid precursor composition substantially or essentially consisting of Ni($^i$Pr-DAD)$_2$ only has not been reported previously. By comparing the NMR spectra of the liquid precursor compositions obtained in the above Examples and Comparative Examples, it is clear that the methods of the present invention is advantageous in obtaining a liquid composition substantially or essentially consisting of Ni($^i$Pr-DAD)$_2$.

Example 7: Layer Deposition by CVD Using Liquid Precursor Composition Containing Co($^i$Pr-DAD)$_2$ Prepared by Example 2

Film deposition was performed by CVD using a liquid precursor composition containing Co($^i$Pr-DAD)$_2$ as prepared by Example 2. A silicon wafer covered by a titanium nitride (TiN) film was used as a substrate. The substrate was placed in a deposition chamber of a reactor, and a temperature of a substrate heater, on which the substrate was placed, was maintained in a range of from 240° C. to 300° C. The liquid precursor composition was placed in a stainless steel container. While the container was heated at 100° C., the liquid precursor composition was evaporated using argon (Ar) as a carrier gas having a flow rate of 60 standard cubic centimeters per minute (sccm). The pressure of the deposition chamber was maintained at 0.5 torr. The vapor of the liquid precursor composition carried by Ar and an ammonia (NH$_3$) gas at a flow rate of 60 sccm were alternatively supplied into the deposition chamber to be brought onto the heated substrate. A gas supply cycle consisting of the liquid precursor composition supply for 20 seconds, Ar gas flow for 10 seconds, NH$_3$ gas flow for 10 seconds, and Ar gas flow for 10 seconds was repeated 300 times to deposit a cobalt-containing layer.

The cobalt-containing layer deposited at the substrate heater temperature of 240° C. was analyzed by Auger electron spectroscopy to measure an atomic content depending on a depth of the film. The depth-profile analysis result was shown in FIG. 21.

Comparative Example 4: Layer Deposition by CVD Using Liquid Precursor Composition Containing Co($^i$Pr-DAD)$_2$ Prepared by Comparative Example 1

Figure 22:
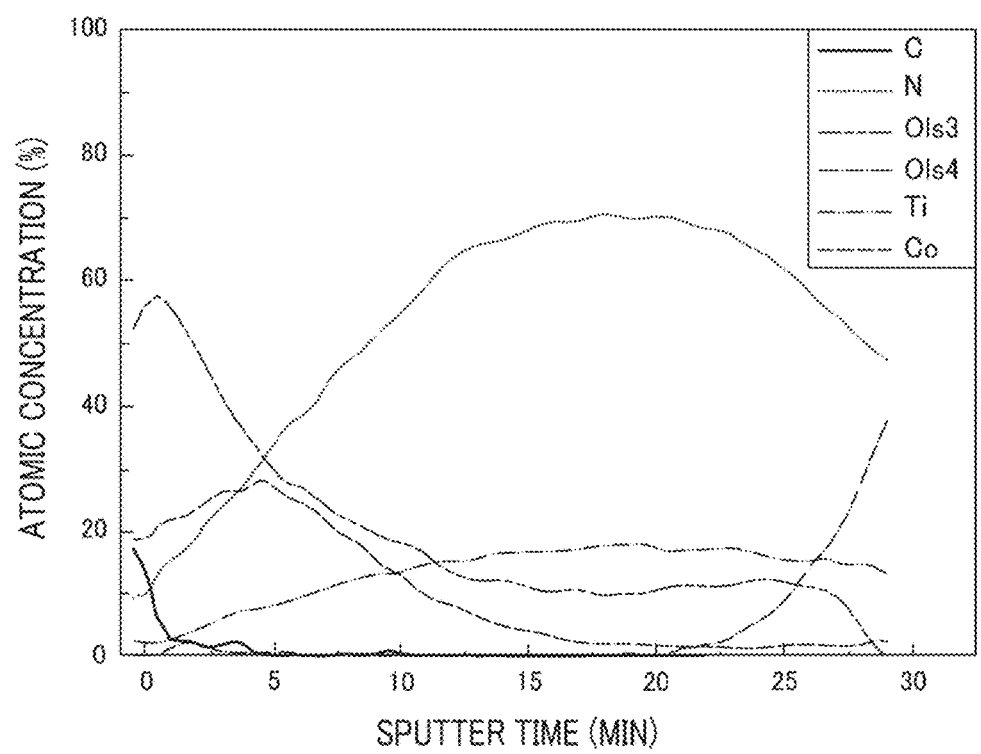
FIG. 22 shows an analysis result of an atomic composition depending on a depth of a layer deposited in accordance with Comparative Example 4 using Auger electron spectroscopy.

Film deposition was performed by CVD using the liquid precursor composition prepared by Comparative Example 1. A deposition condition was the same as Example 7. Further, the prepared layer was analyzed by Auger electron spectroscopy to measure an atomic content depending on a depth of the film. The depth-profile analysis result was as shown in FIG. 22.

Example 8: Layer Deposition by CVD Using Liquid Precursor Composition Containing Ni($^i$Pr-DAD)$_2$ Prepared by Example 4

Film deposition was performed by CVD using the liquid precursor composition containing Ni($^i$Pr-DAD)$_2$ and prepared by Example 4. A silicon wafer covered by a titanium (Ti) film and a gold (Au) film was used as a substrate. The substrate was placed in a deposition chamber of a reactor, and a temperature of a substrate heater, on which the substrate was placed, was maintained in a range of from 160° C. to 200° C. The liquid precursor composition was placed in a stainless steel container. While the container was heated at 90° C., the liquid precursor composition was evaporated using Ar as a carrier gas having a flow rate of 60 sccm. The pressure of the deposition chamber was maintained at 0.5 torr. The vapor of the liquid precursor composition carried by Ar and a hydrogen (H$_2$) gas at a flow rate of 60 sccm were alternatively supplied into the deposition chamber to be brought into contact with the heated substrate. A gas supply cycle consisting of the liquid precursor composition supply 20 seconds, Ar gas flow 10 seconds, H$_2$ gas flow 10 seconds, and Ar gas flow 10 seconds was repeated 100 times to deposit a layer.

The nickel-containing layer deposited at the substrate heater temperature of 160° C. was analyzed by Auger electron spectroscopy to measure an atomic content depending on a depth. The depth-profile analysis result was shown in FIG. 23. A surface and a cross section of the nickel-containing layer deposited at the substrate heater temperature of 200° C. was observed by scanning electron microscopy (SEM), and the results thereof were as shown in FIG. 24A and FIG. 24B.

Comparative Example 5: Layer Deposition by CVD Using Liquid Precursor Composition Containing Ni($^i$Pr-DAD)$_2$ Prepared by Comparative Example 2

Film deposition was performed by CVD using the liquid precursor composition prepared by Comparative Example 2. A deposition condition was the same as Example 8. No deposition of any layer was observed.

Example 9: Cobalt Oxide Layer Deposited by ALD Using Liquid Precursor Composition Containing Co($^i$Pr-DAD)$_2$ Prepared by Example 2

Figure 25:
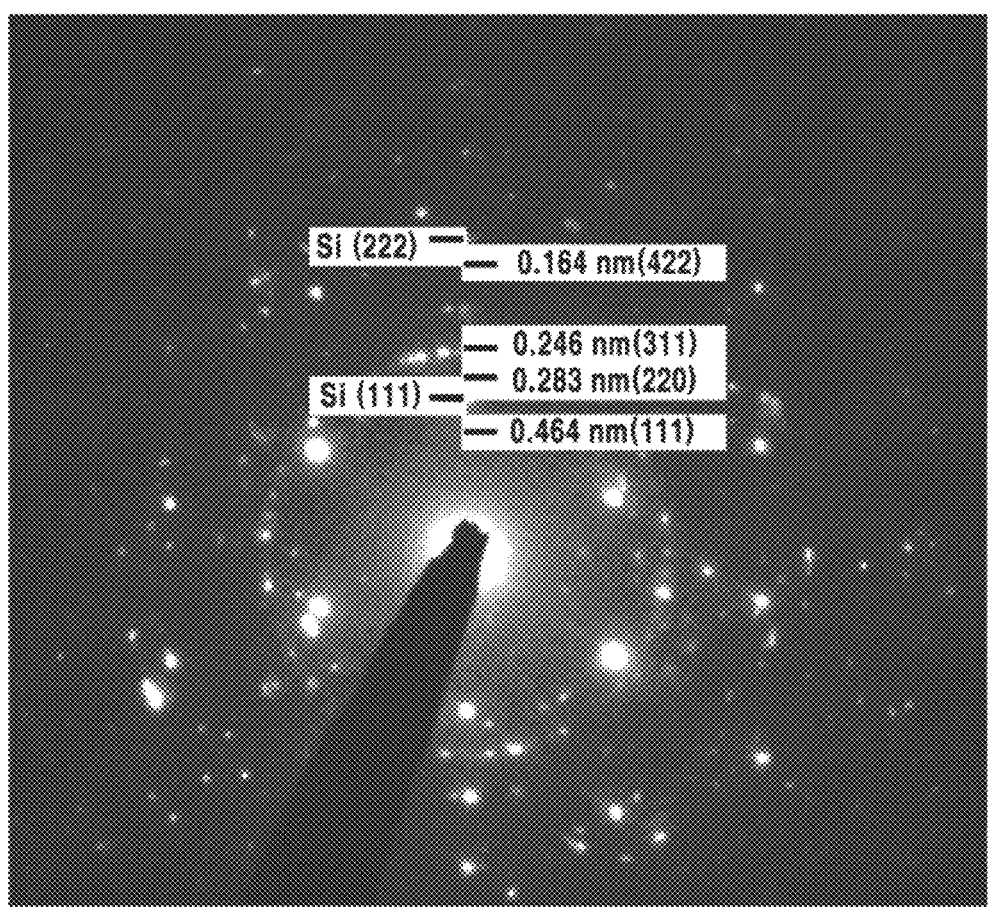
FIG. 25 shows a tunneling electron microscopy (TEM) diffraction pattern image of the cobalt oxide layer deposited in accordance with Example 9.

Cobalt oxide film was deposited by ALD using the liquid precursor composition containing Co($^i$Pr-DAD)$_2$ as prepared by Example 2 and ozone (O$_3$) gas inside a hot wall tube furnace reactor. The liquid precursor composition was vaporized at 65° C. and the vapor was delivered into the chamber with an Ar carrier gas at a flow rate of 50 sccm. The temperature of the gas delivery line was gradually increased from 80 to 110° C. The concentration of O$_3$ generated by an ozone generator was 11%. Ar gas was used as the purge gas at a flow rate of 500 sccm. The ALD window (region of constant growth per cycle) was found between 120 to 250° C. and the growth-per-cycle is 0.12 nm/cycle. FIG. 25 shows a tunneling electron microscopy (TEM) diffraction pattern image of the cobalt oxide film prepared at 250° C. The interplanar spacings of the cobalt oxide film were 0.464, 0.283, 0.246, and 0.164 nm, each corresponding to the (111), (220), (311), and (422) planes of Co$_3$O$_4$ (JCPDS No. 80-1534). No peaks corresponding to the planes of CoO (JCPDS No. 75-0533) were observed. A liquid precursor composition containing Co($^i$Pr-DAD)$_2$ enables ALD of Co$_3$O$_4$, which was not been reported previously. It is because the superior thermal stability of Co($^i$Pr-DAD)$_2$ allows higher ALD process temperature compared to previously used dicobalt hexacarbonyl tert-butylacetylene (CCTBA) or cyclopentadielycobalt dicarbonyl [(C$_5$H$_5$)Co(CO)$_2$].

Figure 21:
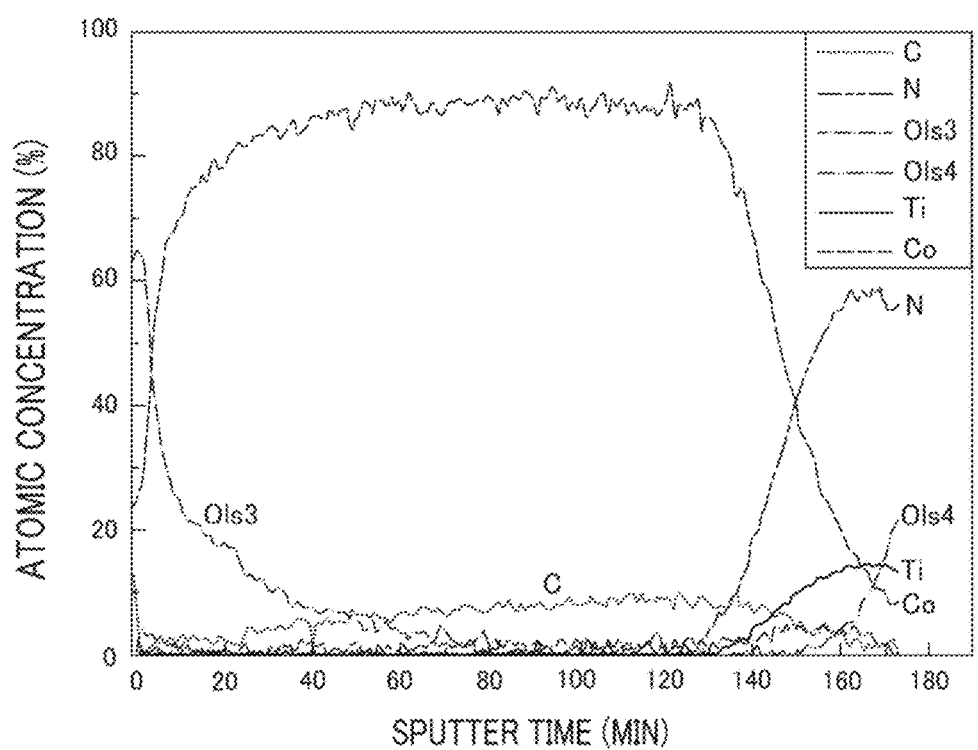
FIG. 21 shows an analysis result of an atomic composition depending on a depth of a cobalt-containing layer deposited in accordance with Example 7 using Auger electron spectroscopy.

FIG. 21 shows an analysis result of an atomic composition depending on a depth of the cobalt-containing layer deposited in accordance with Example 7 using Auger electron spectroscopy, and FIG. 22 shows an analysis result of an atomic composition depending on a depth of the layer deposited in accordance with Comparative Example 4 using Auger electron spectroscopy. Referring to FIG. 21, titanium (Ti) and nitrogen (N) was not detected during 120-minute sputtering for the layer deposited by Example 7 using the liquid precursor composition prepared by Example 2. Thus, it could be seen that a metallic cobalt layer having a cobalt content of about 90 at % was formed on a TiN substrate. Referring to FIG. 22, nitrogen was detected at the surface of the layer deposited by Comparative Example 4 using the liquid precursor composition prepared by Comparative Example 1. Thus, it could be seen that the TiN substrate was not completely covered by the cobalt-containing layer. Further, referring to FIG. 22, after 15-minute sputtering, the Co content decreased to near 0 at %; and the layer consisted of mainly Ti, N, and O. Thus, it could be seen that most of the deposited layer was removed after 15-minute sputtering and the TiN substrate was exposed, which contrasted with the result as shown in FIG. 21 in which a Co content was about 90 at % until 120-minute sputtering. By comparison in result between FIG. 21 and FIG. 22, it can be seen that the layer deposited in Example 7 is much thicker even though the deposition conditions were the same. Thus, it can be concluded that a liquid precursor composition containing 90% or more of Co($^i$Pr-DAD)$_2$ in accordance with the present disclosure is superior to form a cobalt-containing layer compared to a liquid precursor composition containing less than 60% of Co($^i$Pr-DAD)$_2$ with respect to the layer growth rate and the Co content in the deposited layer.

Figure 23:
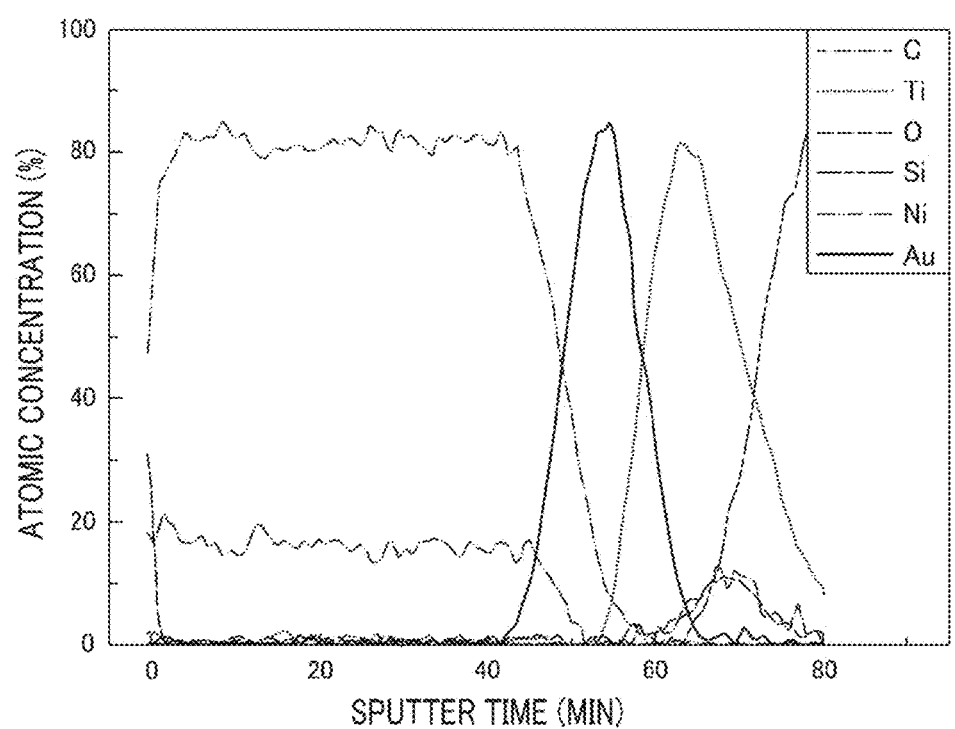
FIG. 23 shows an analysis result of an atomic composition depending on a depth of a nickel-containing layer deposited in accordance with Example 8 using Auger electron spectroscopy.
Figure 24A:
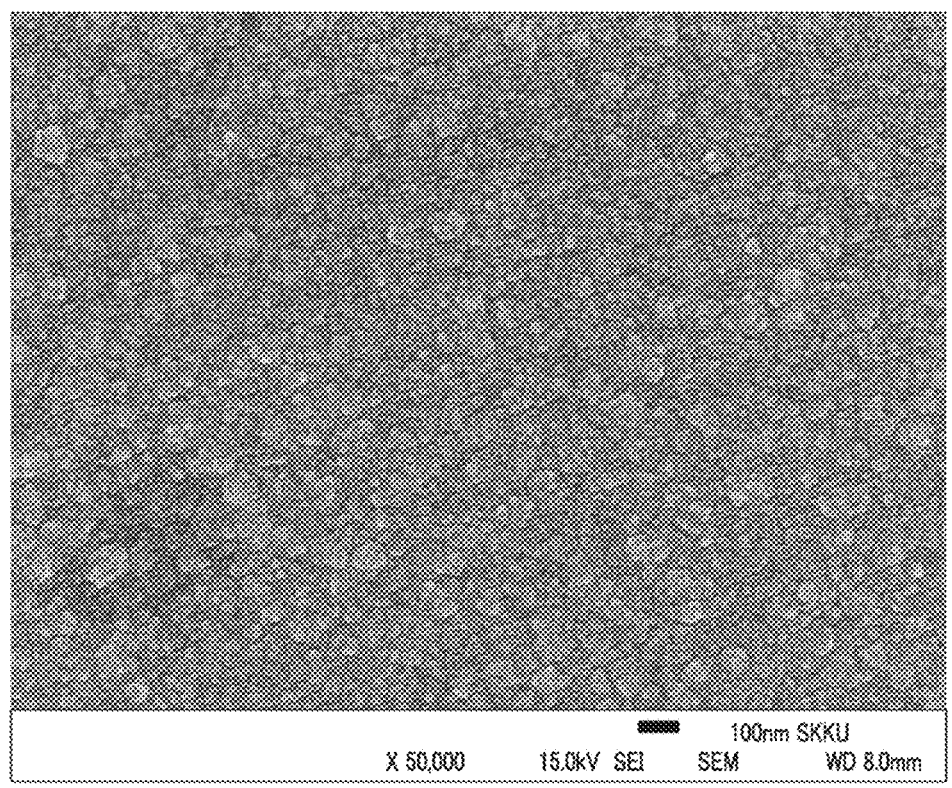
FIG. 24A and FIG. 24B are scanning electron microscopic images of a surface and a cross section of the nickel-containing layer deposited in accordance with Example 8.
Figure 24B:
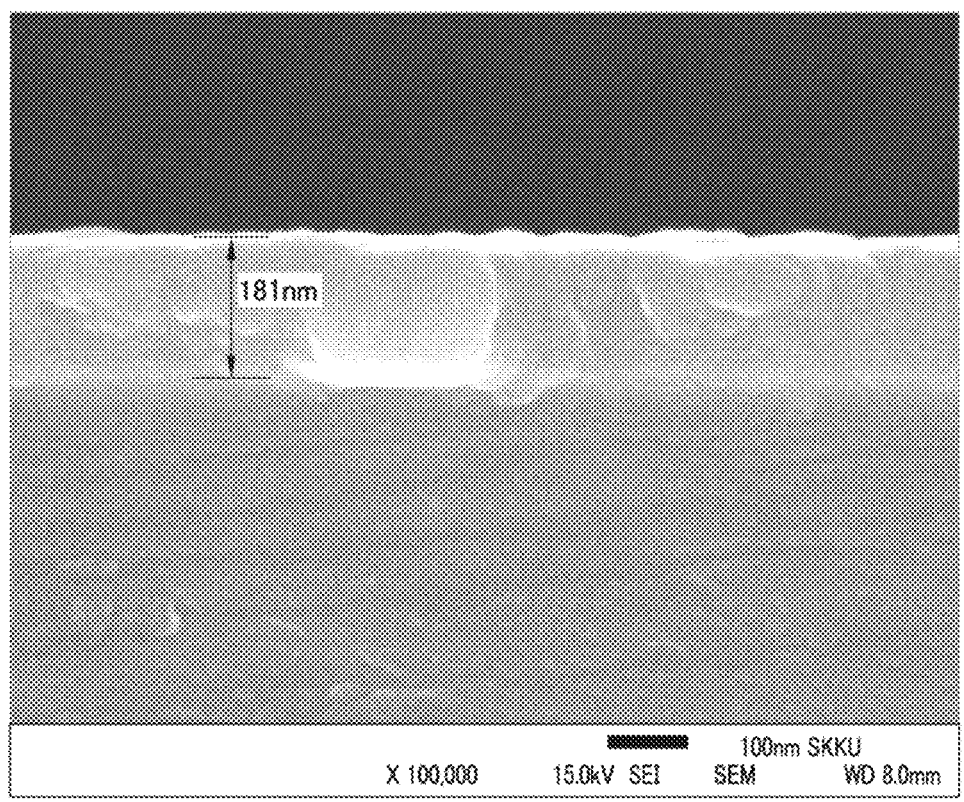

Referring to FIG. 23 showing an Auger depth-profile analysis result a nickel-containing layer deposited in accordance with Example 8, it can be seen that a layer having a nickel content of about 80 at % is formed on the substrate. Referring to FIG. 24A and FIG. 24B showing SEM images of a surface and a cross section of the deposited layer, it can be seen that the substrate is completely covered by a metallic nickel layer having a thickness of 181 nm. Accordingly, it can be seen that a liquid precursor composition according to the present disclosure is suitable to form a nickel-containing layer.

According to the generally known CVD or ALD, a metal oxide layer can be formed using a reactive gas including oxygen and a metal nitride layer can be formed using a reactive gas including nitrogen. By way of example, a cobalt oxide layer or a nickel oxide layer can be formed using the liquid precursor composition of the present disclosure and an oxygen (O$_2$) gas. A cobalt oxide layer or a nickel oxide layer can be formed using the liquid precursor composition of the present disclosure and an ozone (O$_3$) gas. Further, a cobalt nitride layer or a nickel nitride layer can be formed using the liquid precursor composition of the present disclosure and an ammonia (NH$_3$) gas. When a metal film, a metal oxide film, or a metal nitride film is formed, plasma CVD or plasma ALD using plasma may be used.

Experimental Example 1: Thermogravimetry Analysis and Differential Scanning Calorimetry A thermogravimetry (TG) analysis result and a differential scanning calorimetry (DSC) analysis result of the liquid precursor composition prepared in accordance with Example 1 were as shown in FIG. 26 and FIG. 27, respectively.

Figure 26:
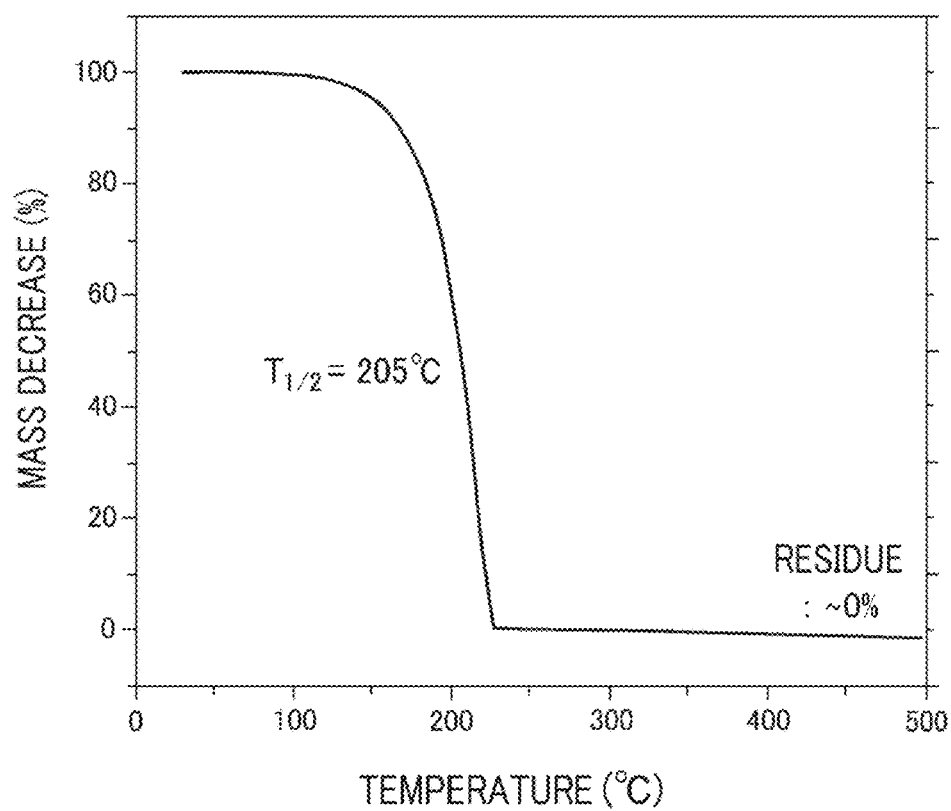
FIG. 26 shows a thermogravimetry analysis (TGA) result of a liquid precursor composition prepared in accordance with Example 1.
Figure 27:
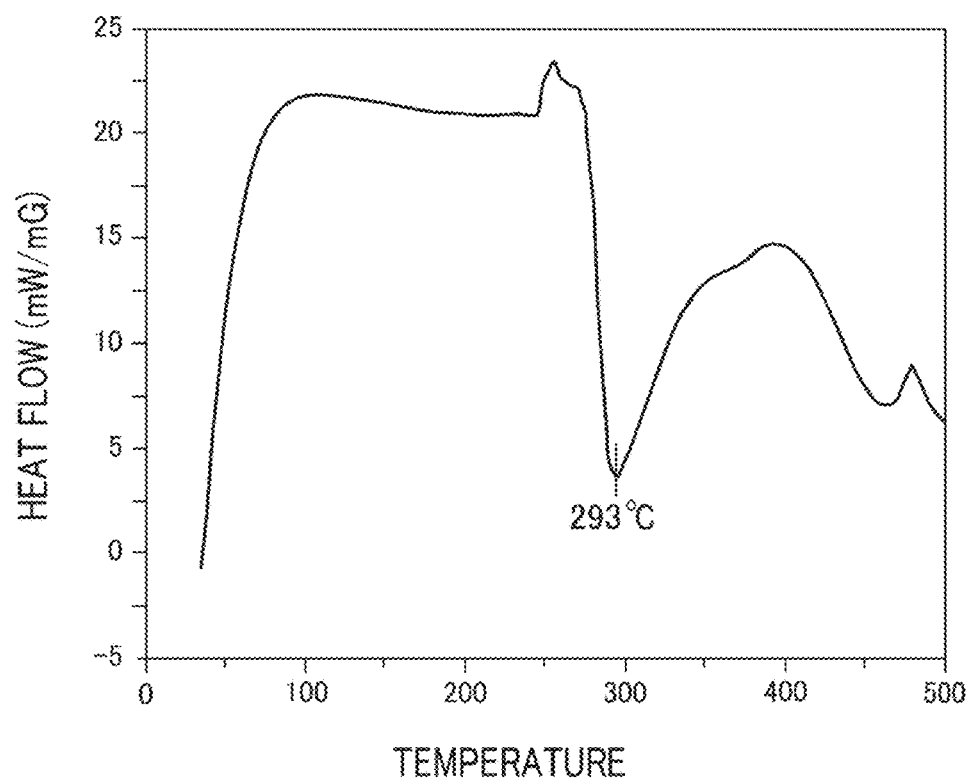
FIG. 27 shows a differential scanning calorimetry (DSC) analysis result of the liquid precursor composition prepared in accordance with Example 1.

FIG. 26 shows a thermogravimetry analysis result of the liquid precursor composition prepared in accordance with Example 1, and FIG. 27 shows a differential scanning calorimetry analysis result of the liquid precursor composition prepared in accordance with Example 1. As shown in FIG. 26, the liquid precursor composition prepared by Example 1 shows abrupt mass decrease at a temperature range of from about 150° C. and about 220° C., and T$_{1/2}$ corresponding to a temperature at which a mass decrease depending on a temperature reaches half the mass of an original sample is 205° C. As shown in FIG. 27, the liquid precursor composition prepared by Example 1 shows a heat-absorption (endothermic) peak at 293° C. caused by decomposition of the compound in the DSC graph.

The above description of the present disclosure is provided for the purpose of illustration, and it would be understood by those skilled in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

What is claimed is:

1. A liquid precursor composition, comprising:
a metal compound represented by the following Chemical Formula 1:

M(DAD)$_2$;  <Chemical Formula 1> wherein in the Chemical Formula 1,
M denotes Co, and
DAD denotes a diazadiene ligand compound represented by R$^1$NC(R$^3$)C(R$^4$)NR$^2$,
wherein R$^1$ and R$^2$ are isopropyl groups and R$^3$ and R$^4$ are independently H or a linear or branched C$_{1-5}$ alkyl group; and
wherein the liquid precursor composition comprises 90% or more of the metal compound,
wherein the liquid precursor composition is liquid at room temperature.

2. The composition of claim 1,
wherein the metal compound is 95% or more of the liquid precursor composition.

3. The composition of claim 1,
wherein the metal compound is Co($^i$PrNCHCHN$^i$Pr)$_2$.

4. The composition of claim 1,
wherein the composition comprises less than 10% impurities.

5. The composition of claim 1,
wherein the composition consists essentially of the metal compound.

6. The composition of claim 1, wherein the molecular weight of the metal compound is 339 g/mol.

7. A method for preparing a liquid precursor composition, comprising:
reacting a mixture containing a halogenated metal compound represented by MX$_2$ or halogenated metal complex compound represented by ZMX$_2$, a diazadiene ligand compound (DAD compound), and an alkali metal in a solvent, followed by purification to obtain a liquid precursor composition containing a metal compound represented by the following Chemical Formula 1:

$$M(DAD)_2;  \quad \text{<Chemical Formula 1>}$$

wherein,

M denotes Co, and

DAD denotes the diazadiene ligand compound represented by $R^1NC(R^3)C(R^4)NR^2$, wherein $R^1$ and $R^2$ are isopropyl groups and R3 and R4 are independently H or a linear or branched alkyl group of $C_{1-5}$;

X is a halogen; and

Z is one or more neutral ligands, wherein in forming the mixture the DAD compound and alkali metal are not combined prior to the combination of either (a) the DAD compound with the halogenated metal compound or halogenated metal complex compound or (b) the alkali metal with the halogenated metal compound or halogenated metal complex compound and wherein the liquid precursor composition comprises 90% or more of the metal compound, and wherein the liquid precursor composition is liquid at room temperature.

8. The method of claim 7, wherein the neutral ligand is one or more of DME, THF, 2-methoxyethyl ether, ammonia, pyridine, N,N,N',N'-tetramethyl-1,2-ethylenediamine, tricyclohexylphosphine, triphenylphosphine, 1,2-Bis(diphenylphosphino)ethane, or 1,3-Bis(diphenylphosphino)propane.

9. The method of claim 7, wherein the mixture is obtained by mixing the halogenated metal compound represented by $MX_2$ or halogenated metal complex compound represented by $ZMX_2$ with the DAD compound, and then subsequently adding the alkali metal.

10. The method of claim 7, wherein the mixture is obtained by mixing the halogenated metal compound represented by $MX_2$ or halogenated metal complex compound represented by $ZMX_2$ with the alkali metal, and then subsequently adding the DAD compound.

11. The method of claim 7, wherein the liquid precursor composition comprises less than 10% impurities.

12. The method of claim 7, wherein the composition consists essentially of the metal compound.

13. The method of claim 7, wherein the metal compound is $Co(^iPrNCHCHN^iPr)_2$.

* * * * *